Figure 1:
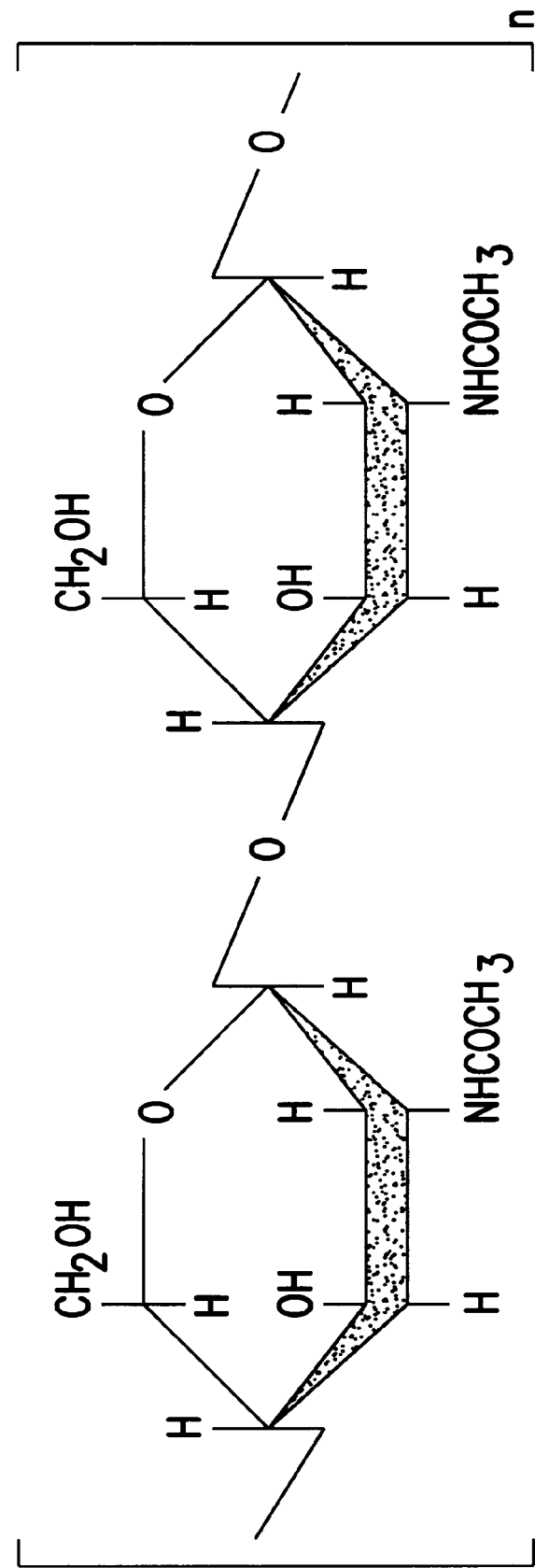

United States Patent [19]

Vournakis et al.

[11] Patent Number: 6,063,911
[45] Date of Patent: May 16, 2000

[54] METHODS AND COMPOSITIONS FOR TREATMENT OF CELL PROLIFERATIVE DISORDERS

[75] Inventors: John N. Vournakis, Charleston, S.C.; Sergio Finkielsztein, Chestnut Hill; Ernest R. Pariser, Belmont, both of Mass.

[73] Assignee: Marine Polymer Technologies, Inc., Danvers, Mass.

[21] Appl. No.: 09/218,288

[22] Filed: Dec. 22, 1998

Related U.S. Application Data

[63] Continuation-in-part of application No. 08/471,290, Jun. 6, 1995, Pat. No. 5,858,350, which is a continuation-in-part of application No. 08/347,911, Dec. 1, 1994, Pat. No. 5,623,064, which is a continuation-in-part of application No. 08/160,569, Dec. 1, 1993, Pat. No. 5,622,834.

[51] Int. Cl.$^7$ ............................ C08B 37/08; C12P 19/26; A61K 31/73
[52] U.S. Cl. ........................... 536/20; 536/55.2; 424/488; 424/499; 435/84; 514/55
[58] Field of Search .................... 536/20, 55.2; 424/488, 424/499; 435/84; 514/55

[56] References Cited

U.S. PATENT DOCUMENTS

| | | |
|---|---|---|
| 3,988,411 | 10/1976 | Capozza . |
| 3,989,535 | 11/1976 | Capozza . |
| 4,378,017 | 3/1983 | Kosugi et al. . |
| 4,749,620 | 6/1988 | Rha et al. . |
| 4,803,168 | 2/1989 | Jarvis, Jr. . |
| 4,942,129 | 7/1990 | Goosen et al. . |
| 5,008,116 | 4/1991 | Cahn . |
| 5,071,977 | 12/1991 | Cassels et al. . |
| 5,116,747 | 5/1992 | Moo-Young et al. . |
| 5,219,749 | 6/1993 | Bouriotis et al. . |
| 5,229,123 | 7/1993 | Masubuchi et al. . |
| 5,529,914 | 6/1996 | Hubbell et al. . |
| 5,550,110 | 8/1996 | Cody et al. . |
| 5,573,934 | 11/1996 | Hubbell et al. . |
| 5,622,834 | 4/1997 | Vournakis et al. . |
| 5,623,064 | 4/1997 | Vournakis et al. . |
| 5,624,679 | 4/1997 | Vournakis et al. . |
| 5,641,752 | 6/1997 | Cody et al. . |
| 5,658,943 | 8/1997 | Berryman et al. . |
| 5,858,350 | 1/1999 | Vournakis et al. . |

FOREIGN PATENT DOCUMENTS

| | | |
|---|---|---|
| 2072395 | 1/1993 | Canada . |
| 0 543 572 | 5/1993 | European Pat. Off. . |
| 55-152705 | 11/1980 | Japan . |
| 62-288602 | 12/1987 | Japan . |
| 1038367 | 8/1966 | United Kingdom . |
| WO 93/08799 | 5/1993 | WIPO . |
| WO 93/09176 | 5/1993 | WIPO . |
| WO 93/12875 | 7/1993 | WIPO . |
| WO 94/03483 | 2/1994 | WIPO . |
| WO 96/11927 | 4/1996 | WIPO . |
| WO 97/08169 | 3/1997 | WIPO . |
| WO 97/37987 | 10/1997 | WIPO . |

OTHER PUBLICATIONS

Zielinski and Aebischer, 1994, "Chitosan as a matrix for mammalian cell encapsulation", Biomaterials 15(13):1049–1056.

Vournakis et al., 1994, "Isolation & characterization of pure poly–N–acetylglucosamine: Controlled enzymatic deacetylation and formulation for tissue engineering applications", J Cell Biochem Suppl O, No. 18C, p. 283 Abstract PZ 313, Keystone Symposium on Tissue Engineering.

Polk, A. et al., 1994, J. of Pharmaceutical Sciences, 83(2):178–185.

Matthew et al., 1993, "Complex coacervate microcapsules for mammalian cell culture and atificial organ development", Biotechnol Prog 9(5):510–519.

Groboillot et al., 1993, "Membrane formation by interfacial cross–linking of chitosan for microencapsulation of *Lactococcus lactis*", Biotechnology and Bioengineering 42(10):1157–1163.

Aebisher, P. et al., 1993, in "Fundamentals of Animal Cell Encapsulation and Immobilization", CRC Press, pp. 197–224.

Mireles, C. et al., 1992, in "Advances in Chitin and Chitosan", Brine, C.J. et al., eds., Elsevier Publishers, Ltd., pp. 506–515.

Thanoo et al., 1992, "Cross–linked chitosan microspheres: Preparation and evaluation as a matrix for the controlled release of pharmaceuticals", J. Pharm. Pharmacol., 44, 283–286.

Dong, C. and Rogers, J.A., 1991, Journal of Controlled Release, 17:217–224.

US Pharmacopeia XXII, 1991, Supplement 5, pp. 2702–2703.

Hirano et al., 1990, "The Regulation of Serum Cholesterol Level by Oral Administration of Chitosan in Rabbits", in: *Proceedings of the International Symposium on Chitin Derivatives in Life Sciences*, Oct. 5–7, pp. 115–120.

Kurita, K. et al., 1990, "Preparations of soluble chitin derivatives and the modifications to branched chitins" Polym. Prep. (Am. Chem. Soc., Div. Polym. Chem.) 31:624–625.

(List continued on next page.)

*Primary Examiner*—Leon B. Lankford, Jr.
*Assistant Examiner*—Christopher R. Tate
*Attorney, Agent, or Firm*—Pennie & Edmonds LLP

[57] ABSTRACT

The present invention relates to methods and compositions comprising at least one endothelin antagonist, preferably in combination with a poly-β-1→4-N-acetylglucosamine (p-GlcNAc) polysaccharide matrix, for use in the treatment of cancer and other proliferative diseases. The endothelin antagonist can be a peptide or non-peptide compound, and the p-GlcNAc matrix of the invention is comprised of a polymer of high molecular weight whose constituent monosaccharide sugars are attached in a β-1→4 conformation, and which is free of proteins, and substantially free of single amino acids, and other organic and inorganic contaminants. The compositions and methods of the invention are useful for inhibiting the growth of tumors and other neoplastic cells and/or for inhibiting the metastasis of neoplastic cells in vivo.

35 Claims, 12 Drawing Sheets

OTHER PUBLICATIONS

Yoshioke, T. et al., 1990, Biotechnol Bioeng. 35:66–72.
US Pharmacopeia XXII, 1990, pp. 1415–1497.
US Pharmacopeia XXII, 1990, 1497–1500.
Kurita, K. and Inoue, S., 1989, in "Chitin and Chitosan", Skjak–Braek et al., eds., Elsevier Science Publishing Co., Inc., p. 365–372.
Bedemeier et al., 1989, Pharm. res., 6(5), 413–417.
Hirano, S., 1989, "Production and application of chitin and chitosan in Japan," in "Chitin and Chitosan," Skjak–Braek, Anthonsen, and Sanford, eds. Elsevier Science Publishing Co., pp. 37–43.
Maresh, G. et al., 1989, "Hydroxypropylation of chitosan," "Chitin and Chitosan," Skjak–Braek, Anthonsen, and Sanford, eds. Elsevier Science Publishing Co., pp. 389–395.
Blackwell, 1988, Meth. Enz., 161, 435–442.
Austin, P.R. and Sennett, S., 1986, "Dry chitosan salts and complexes of aliphatic carboxylic acids," in "Chitin in Nature and Technology," Muzzarelli et al., eds. Plenum Press, New York, pp 497–506.
Komai, T. et al., 1986, "Biomedical evaluation of acylated chitins as coating materials," in "Chitin in Nature and Technology," Muzzarelli et al., eds. Plenum Press, New York, pp 497–506.
Nishi, N. et al., 1986, "Preparation and characterization of phosphorylated chitin and chitosan," in "Chitin in Nature and Technology," Muzzarelli et al., eds. Plenum Press, New York, pp 297–299.
Domard, A., 1986, "Circular dichroism study on N–acetyl-glucosamine oligomers," Int. J. Macromol. 8:243–246.
Statos, J.V., et al., 1986, "Enhancement by N–hydroxysulfosuccinate of water soluble carbodiimide mediated coupling reactions," Anal. Biochem. 156:220–222.
Hwang, C. et al., 1985, "Encapsulation with Chitosan: Transmembrane Diffusion of Proteins in Capsules," in Muzzareli, R. et al., eds., "Chitin in Nature and Technology", Plenum Press, pp. 389–396.
Vahouny, G.V., 1983, Journal of Clinical Nutrition, 38:278–284.
Tokura, S. et al., 1983, "Studies on chitin VIII. Some properties of water soluble chitin derivatives," Polym. J. 15:485–489.
Davis, M. and Preston, J.F., 1981, "A simple modified carbodiimide method for conjugation of small molecular weight compounds to immunoglobulin G with minimal protein crosslinking," Anal. Biochem. 116:402–407.
Hirano, S. et al., 1981, "SEM ultrastructure studies of N–acyl– and N–benzylidene–chitosan membranes," J. Biomed. Mat. Res. 15:903–911.
Berkeley et al., 1979, "Chitin, Chitosan and Their Degradative Enzymes", in: *Microbial Polysaccharides and Polysaccharases*, Berkeley et al., eds., Academic Press, pp. 205–216.
Hirano, S. et al., 1976, "Selective N–acylation of chitosan," Carbohydrate Research 47:315–320.
Schweiger, RG., 1972, "Polysaccharide sulfates I. Cellulose sulfate with a high degree of substitution," Carbohydrate Res. 21:219–228.
Noguchi, J. et al., 1969, "Chitosan epichlorohydrin anion exchange resin with primary amine as absorption site," Kogyo Kagaku Zasshi 72:796–799.
Blackwell et al., 1967, J. Mol. Biol., 28, 383–385.

Falk et al., 1966, "Studies on chitin ($\beta$–(1→4)–linked 2–acetamido–2–deoxy–D–glucan) fibers of the diatom thalassiosira fluviatilis hustedt", Can. J. Chem., 44, 2269–2281.
McLachlan and Craigne, 1966, Some Contemp. Stud. Mar. Sci., 511–517.
McLachlan, A.G. et al, 1965, "Studies on the chitin (chitin: poly–N–acetylglucosamine) fibers of the diatom thalassiosira fluviatilis hustedt," Can. J. Botany 43:707–713.
Schorigin, P. and Hait, E., 1934, Chem. Ber. 67:1712–1714.
"Barriers to Commercialization", Ch. 4 in *Chitin and Chitosan*, Technical Insights, Inc., Ft. Lee, NJ.
Battistini et al., 1993, "Growth Regulatory Properties of Endothelins", Peptides 14:385–399.
Bell et al., 1995, "Effect of Endothelin–1 and Sarafotoxin S6c on Blood Flow in a Rat Tumor", J. Cardiovasc. Physiol. 26(Suppl. 34):S222–S225.
Gomez–Garre et al., 1996, "An Orally Active $ET_A/ET_B$ Receptor Antagonist Ameliorates Proteinuria and Glomerular Lesions in Rats with Proliferative Nephritis", Kidney Intl. 50:962–972.
Halaban, 1996, "Growth Factors and Melanomas", Seminars in Oncology 23:673–681.
Hocher et al., 1997, "The Paracrine Endothelial System: Pathophysiology and Implications in Clinical Medicine", Eur. J. Chem. Clin. Biochem. 35:175–189.
Kenny et al., 1997, "Pharmacological Options in the Treatment of Benign Prostatic Hyperplasia", J. Medicinal Chem. 40:1293–1315.
Kikuchi et al., 1996, "Decreased $ET_B$ Receptor Expression in Human Metastatic Melanoma Cells", Biochem. Biophys. Res. Comm. 219:734–739.
Lundblad et al., 1996, "Granulocyte Colony–Stimulating Factor Improves Survival Rate and Reduces Concentrations of Bacteria, Endotoxin, Tumor Necrosis Factor, and Endothelin–1 in Fulminant Intra–Abdominal Sepsis in Rats", Crit. Care Med. 24:820–826.
Lüscher and Wenzel, 1995, "Endothelin and Endothelin Antagonists: Pharmacology and Clinical Implications", in: *Mediators in the Cardiovascular System: Regional Ischemia*, Birkhäuser Verlag, Basel, Switzerland, pp. 237–253.
Markewitz et al., 1995, "Endothelin–1 Synthesis, Receptors, and Signal Transduction in Alveolar Epithelium: Evidence for an Autocrine Role", Am. J. Physiol. 268:L192–L200.
Mateo and De Artiñano, 1997, "Highlights on Endothelins: A Review", Pharmacol. Res. 36:339–351.
Moraitis et al., 1997, Endothelin Expression and Responsiveness in Human Ovarian Carcinoma Cell Lines, Eur. J. Cancer 33:661–668.
Morbidelli et al., 1995, "Proliferation and Migration of Endothelial Cells is Promoted by Endothelins via Activation of $ET_B$ Receptors", Am. J. Physiol. 269:H686–H695.
Nelson et al., 1996, "Endothelin–1 Production and Decreased Endothelin B Receptor Expression in Advanced Prostate Cancer", Cancer Res. 56:663–668.
Ohlstein et al., 1996, "Endothelin Receptors: Receptor Classification, Novel Receptor Antagonists, and Potential Therapeutic Targets", Medicinal Res. Rev. 16:365–390.
Oikawa et al., 1994, "Production of Endothelin–1 and Thrombomodulin by Human Pancreatic Cancer Cells", Br. J. Cancer 69:1059–1064.
Parris and Webb, 1997, "The Endothelin System in Cardiovascular Physiology and Pathophysiology", Vascular Med. 2:31–43.

Patel and Schrey, 1995, "Human Breast Cancer Cells Contain a Phosphoramidon–Sensitive Metalloproteinase which Can Process Exogenous Big Endothelin–1 to Endothelin–1: A Proposed Mitogen for Human Breast Fibroblasts", Brit. J. Cancer 71:442–447.

Reid et al., 1996, "Multiple Roles for Endothelin in Melanocyte Development: Regulation of Progenitor Number and Stimulation of Differentiation", Development 122:3911–3919.

Shichiri et al., 1991, "Endothelin–1 is an Autocrine/Paracrine Growth Factor for Human Cancer Cell Lines", J. Clin. Invest. 87:1867–1871.

Suzuki et al., 1989, Production of Endothelin–1 and Big–Endothelin–1 by Tumor Cells with Epithelial–Like Morphology, J. Biochem. 106:736–741.

Webb and Meek, 1997, "Inhibitors of Endothelin", Medicinal Res. Rev. 17:17–67.

Yamashita et al., 1991, "A Large Amount of Endothelin–1 is Present in Human Breast Cancer Tissues", Res. Comm. Chem. Pathol. Pharmacol. 74:363–369.

Yanagisawa et al., 1988, "A Novel Potent Vasoconstrictor Peptide Produced by Vascular Endothelial Cells", Nature 332:411–415.

Yohn et al., 1994, "Human Melanoma Cells Express Functional Endothelin–1 Receptors", Biochem. Biophys. Res. Comm. 201:449–457.

Ziche et al., 1995, "$ET_B$ Receptors Promote Proliferation and Migration of Endothelial Cells", J. Cardiovasc. Pharmacol. 26 (Suppl. 3):S284–S286.

B16 $10^{-5}$ cells RO $10^{-7}$ M

B16 $10^5$ cells no RO 6,063,911

METHODS AND COMPOSITIONS FOR TREATMENT OF CELL PROLIFERATIVE DISORDERS

The present application is a continuation-in-part of U.S. application Ser. No. 08/471,290, filed Jun. 6, 1995, now U.S. Pat. No. 5,858,350 which application is a continuation-in-part of U.S. application Ser. No. 08/347,911, filed Dec. 1, 1994, now U.S. Pat. No. 5,623,064, which is a continuation-in-part of U.S. application, Ser. No. 08/160,569, filed Dec. 1, 1993, now U.S. Pat. No. 5,622,834, which applications are incorporated herein by reference in their entireties.

1. INTRODUCTION

The present invention relates to methods and compositions comprising at least one endothelin antagonist, preferably in combination with a poly-$\beta$-1→4-N-acetylglucosamine (p-GlcNAc) polysaccharide matrix, for use in the treatment of cancer and other proliferative diseases. More specifically, the endothelin antagonist of the invention can be a peptide or non-peptide compound, and the p-GlcNAc matrix of the invention is comprised of a polymer of high molecular weight whose constituent monosaccharide sugars are attached in a $\beta$-1→4 conformation, and which is free of proteins, and substantially free of single amino acids, and other organic and inorganic contaminants. The compositions and methods of the invention are useful for inhibiting the growth of tumors and other neoplastic cells and/or for inhibiting the metastasis of neoplastic cells in vivo.

2. BACKGROUND OF THE INVENTION

The endothelins are a family of 21-amino acid peptides, e.g., ET-1, ET-2, and ET-3, originally characterized by their potent vasoconstricting and angiogenic properties (see, e.g., Luscher et al., 1995, Agents Actions Suppl. (Switzerland) 45: 237–253; Yanagisawa et al., 1988, Nature 332: 411–415). These peptides additionally appear to be related to growth factors such as bFGF and often act in synergy with them (see, e.g., Halaban, 1996, Seminars in Oncology 23: 673–681; Reid et al., 1996, Development 122: 3911–3919; Markewitz et al., 1995, Am. J. Physiol. 268: L192-L200; and Nelson et al., 1996, Cancer Res. 56: 663–668). Furthermore, these peptides display cytokine-like regulatory properties and can be influenced by hormones such as insulin and angiotensin II as well as growth factors such as TGF-$\beta$ and TNF-$\alpha$ (Nelson et al., supra; Suzuki et al., 1989, J. Biochem. 106: 736–741; and Lundblad et al., 1996, Crit. Care Med. 24: 820–826; ). Endothelin activity is mediated via binding with preferential affinities to two distinct G-coupled receptors, ETA and ETB, in an autocrine/paracrine manner (see, e.g., Hocher et al., 1997, Eur. J. Clin. Chem. Clin. Biochem. 35(3): 175–189; Shichiri et al., 1991, J. Cardiovascular Pharmacol. 17: S76-S78).

There are a variety of agonists and antagonists of endothelin receptors (Webb et al., supra), which have been used to study the mechanism of action of the endothelins. Because endothelin is known to have powerful vasoconstrictive activity, endothelin antagonists in particular (also termed "endothelin receptor antagonists" in the art) have been studied with regard to their possible role in treating human disease, most notably, cardiovascular diseases such as hypertension, congestive heart failure, atherosclerosis, restenosis, and myocardial infarction (Mateo et al., 1997, Pharmacological Res. 36 (5): 339–351). For example, non-peptide-based endothelin antagonists belonging to the pyrimidinyl sulfonamide family, such as Ro 46-2005 and bosentan, which interact with the endothelin receptor through their aromatic rings, are currently undergoing clinical evaluation for the treatment of hypertension, vascular disease, and congestive heart failure. These antagonists can bind both ETA and ETB with varying affinities and have advantages over peptide-based antagonists because they possess an improved metabolic stability (Webb et al., supra; and Parris et al., supra). In addition, endothelin antagonists have also been studied with regard to their possible role in the treatment of kidney disease such as impaired renal function in liver cirrhosis and acute renal failure (Gomez-Garre et al., 1996, Kidney Int. 50: 962–972; Hocher et al., supra).

More recently, endothelins and endothelin receptors have been implicated in a number of normal and pathological cell growth processes, e.g., cell cycle progression, cell growth, and cellular development (see, e.g., Parris et al., 1997, Vascular Medicine 2: 31–43; Markewitz et al., supra; Morbidelli et al., 1995, Am. J. Physiol. 269: H686-H695; and Battistini et al. 1993, Peptides 14: 385–399). ET1 and ET3 have been shown to be mitogenic and chemokinetic factors for normal tissues ranging from endothelial and epithelial cells to macrophages (see, e.g., Webb et al., 1997, Medicinal Research Reviews 17 (1): 17–67; and Gomez-Garre et al., supra). In addition, the binding of endothelins to their receptors has been shown to cause DNA synthesis, proliferation and cell mobilization in normal and neoplastic cells (Webb et al., supra; Ziche et al., 1995, Cardiovasc. Pharmacol. 26: S284-S286; and Yamashita et al., 1991, Res. Comm. in Chem. Pathol. and Pharmacol. 74 (3): 363–369).

This potential capability of endothelins to mediate cell growth and cell cycle progression has led to some initial studies of endothelin expression and/or endothelin receptor presence in cancer cells. For example, ET-1 has been shown to be overexpressed in breast cancer and pancreatic cell lines and induces proliferation in breast cancer tissue, ovarian cell lines and prostate tumors (see, e.g., Moriatis et al., 1997, Eur. J. Canc. 33 (4): 661–668; Nelson et al., 1996, Cancer Res. 56: 663–668; Patel et al., 1995, Br. J. Cancer 71: 442–447; Oikawa et al., 1994, Br. J. Cancer 69: 1059–1064; Shichiri et al., supra; and Yamashita et al., supra). In addition, the presence of ETA type receptors, which have a higher affinity for ET1 and ET2, has been demonstrated in ovarian cell lines (Moriatis et al., supra) and breast cancer tissues (Yamashita et al., supra). One of the few tumors to express ETB receptors that have a similar affinity for all three isoforms of endothelin is melanoma (Yohn et al., 1994, Biochem. Biophys. Res. Comm. 201 (1): 449–457). Interestingly, ETB receptors are highly expressed in primary or recurrent melanomas but less so in metastatic melanomas (Kikuchi et al., 1996, Biochem. Biophys. Res. Comm. 219: 734–739).

Although these studies suggest that endothelin antagonists could potentially have therapeutic applications in the treatment of cancer, there have been no studies to date demonstrating any such therapeutic application. In fact, the role that endothelin may play in promoting proliferative disease such as various vascular proliferative diseases and benign prostatic hypertrophy (BPH) is unclear (Webb et al., supra and Kenny et al., 1997, J. Med. Chem. 40 (9): 1293–1315). Moreover, while U.S. Pat. Nos. 5,550,110 and 5,641,752 disclose the use of specific hexapeptide endothelin antagonists for the treatment of cancer, there is actually no data in those disclosures relating to cancer treatment and no indication as to how to perform such treatment or indeed whether such treatment would be successful (see also, PCT applications WO 97/37987, 97/08169, WO 96/11927, and WO 94/03483, Canadian patent application 2072395, and U.S. Pat. No. 5,658,943).

3. SUMMARY OF THE INVENTION

The present invention relates to methods and compositions for the treatment of cell proliferative disorders such as cancer. More specifically, the invention relates to compositions comprising at least one endothelin antagonist, preferably in combination with a poly-β-1→4-N-acetylglucosamine (p-GlcNAc) polysaccharide matrix, for use in the treatment of cancer and other proliferative diseases. The present invention is based, in part, on Applicants' discovery that, when an endothelin antagonist is administered in vivo, either alone in high doses or in combination with a polysaccharide matrix, tumor cell growth and/or the growth or metastasis of neoplastic cells are significantly inhibited.

According to a preferred embodiment of the invention, the endothelin antagonist is a non-peptide-based pyrimidyl sulfonamide compound, such as that depicted in FIG. 1 below.

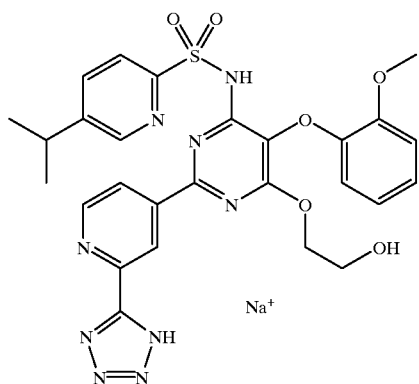

The compound of FIG. 1 is 5-Isopropyl-pyridine-2-sulfonic acid [6-(2-hydroxy-ethoxy)-5-(2-methoxy-phenoxy),-2-[2-(1H-tetrazol-5-yl)-pyridin-4-yl]-pyrimidin-4-yl]amide sodium salt (1:2), also termed herein "Ro61" and has a molecular weight of approximately 650 kD. It is a non-specific, non-peptide inhibitor of both endothelin receptors, ETA and ETB.

According to a preferred embodiment of the invention, the polysaccharide matrix is a poly-β-1→4-N-acetylglucosamine (p-GlcNAc) polysaccharide matrix, or a derivative thereof, as described in U.S. Pat. No. 5,635,493, which is incorporated herein by reference in its entirety. The p-GlcNAc or its derivatives may be utilized in various reformulations, including membranes, filaments, non-woven textiles, sponges, gels and three-dimensional matrices. According to a preferred embodiment, the p-GlcNAc is in the form of a gel, is preferably deacetylated and optionally, derivatized to a p-GlcNAc-lactate salt, and is combined with Ro61 for administration in vivo.

The compositions of the invention are useful for drug delivery systems, e.g., slow-release drug delivery. The compositions of the invention are an improvement over traditional drug formulations in that the compositions of the invention provide, for example, increased effectiveness, reduced toxicity and improved bioavailability.

The methods of the invention comprise the administration of therapeutically effective amounts of the compositions of the invention in vivo for the treatment of cell proliferative diseases such as cancer in an animal, including humans. According to one embodiment of the invention, at least one endothelin antagonist, such as Ro61, is dissolved in a deacetylated p-GlcNAc-lactate gel and administered, in a therapeutically effective amount, to a patient in vivo for the treatment of cancer or other proliferative diseases or disorders. Another embodiment of the invention comprises the administration in vivo of an endothelin antagonist, more preferably, a non-peptide-based endothelin antagonist such as a pyrimidyl sulfonamide endothelin antagonist, for the treatment of cancer or other proliferative diseases or disorders. Yet another embodiment of the invention comprises the administration in vivo of a p-GlcNAc matrix alone for the treatment of cancer or other proliferative diseases or disorders. The compositions and methods of the invention are useful for the inhibition of tumor and/or other neoplastic cell growth and/or the inhibition of metastasis of neoplastic cells in vivo.

4. BRIEF DESCRIPTION OF THE FIGURES

FIG. 1. Chemical structure of 100% p-GlcNAc. "in" refers to an integer ranging from about 4,000 to about 150,000, with about 4,000 to about 15,000 being preferred.

Figure 2:
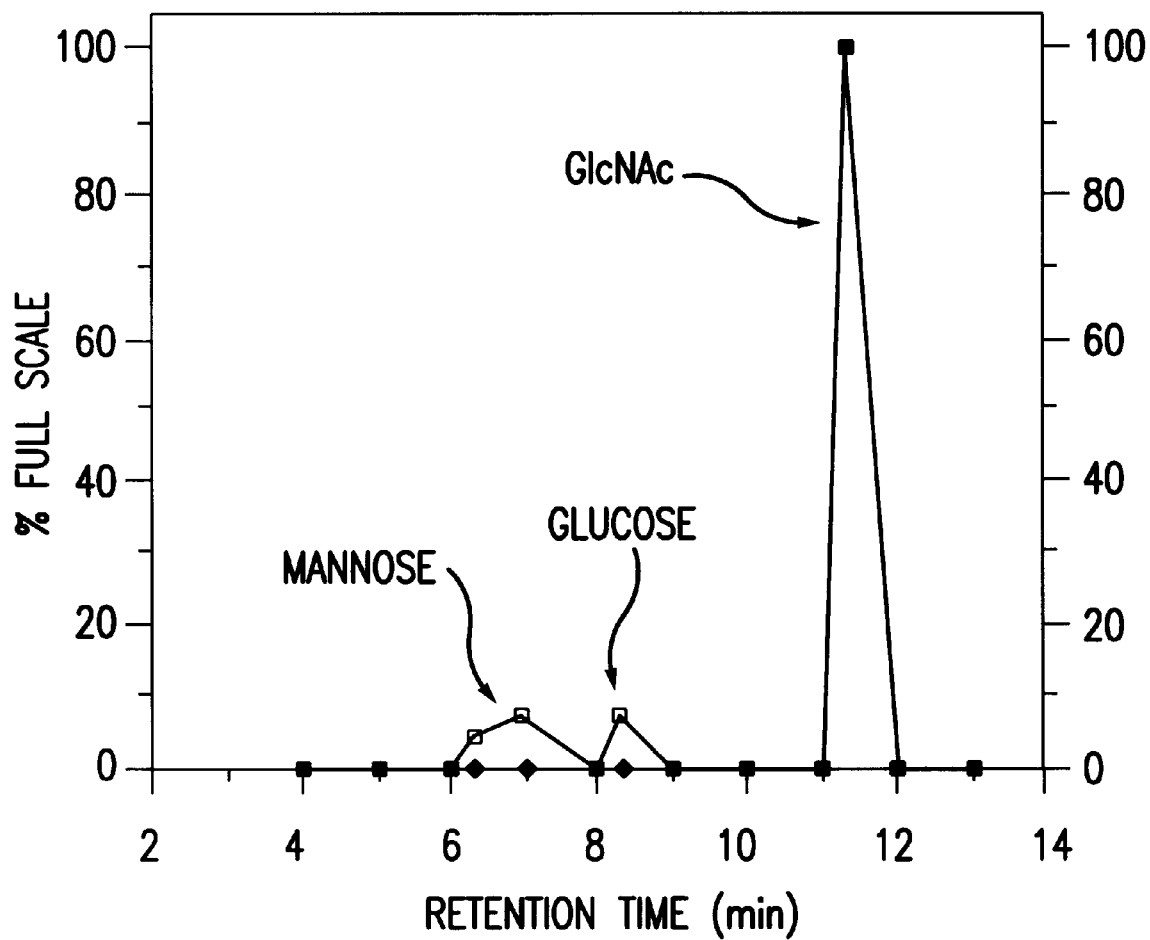

FIG. 2. Carbohydrate analysis of p-GlcNAc, Gas Chromatography-Mass Spectroscopy data. Solid squares represent p-GlcNAc purified using the acid treatment/neutralization method described in Section 5.1, infra.

Figure 3:
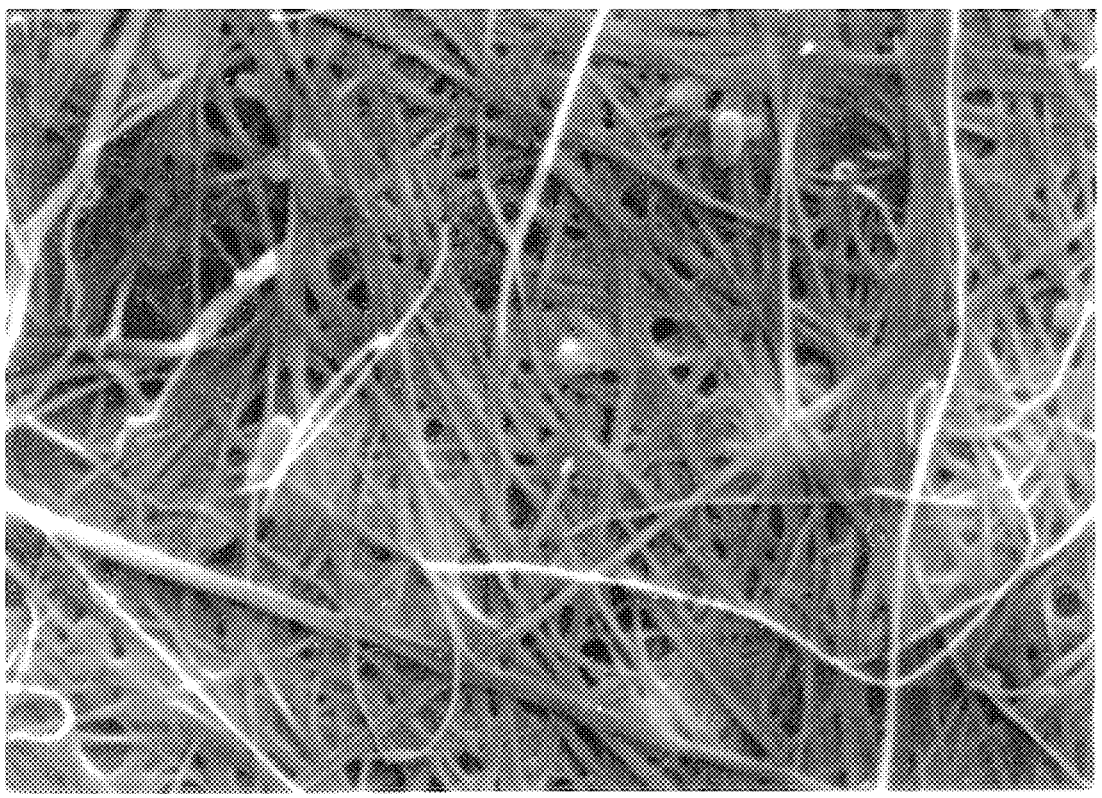

FIG. 3. Scanning electron micrograph depicting a p-GlcNAc membrane prepared by the acid treatment/neutralization variation of the chemical/biological purification method. Magnification: 10,000×.

Figure 4:
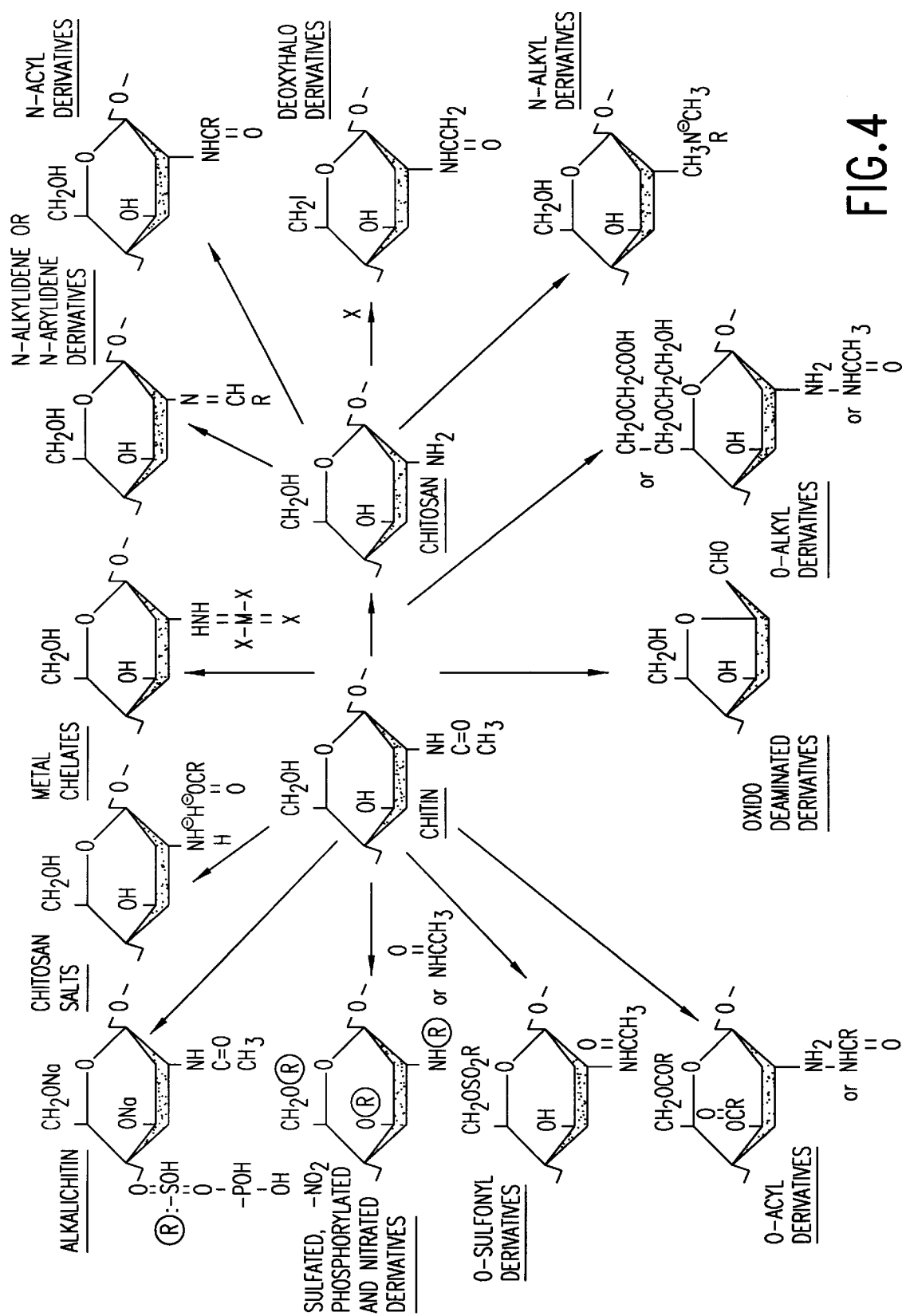

FIG. 4. Diagram depicting some of the possible p-GlcNAc and deacetylated p-GlcNAc derivatives of the invention (Adapted from S. Hirano, In "Chitin and Chitosan", 1989, Skjak-Braek, Anthonsen, and Sanford, eds., Elsevier Science Publishing Co., pp. 37–43).

Figure 5A:
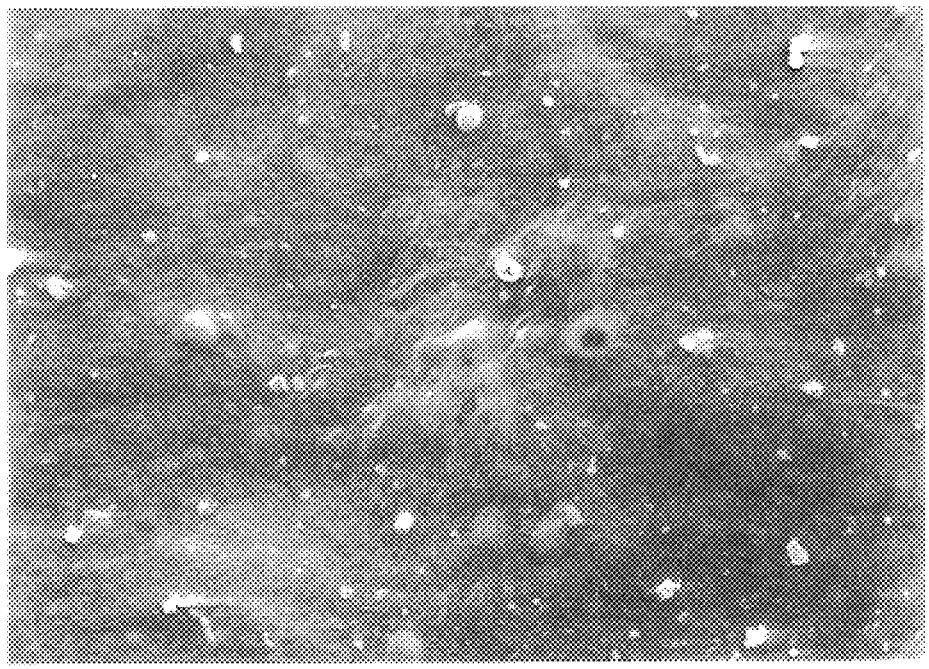
Figure 5B:
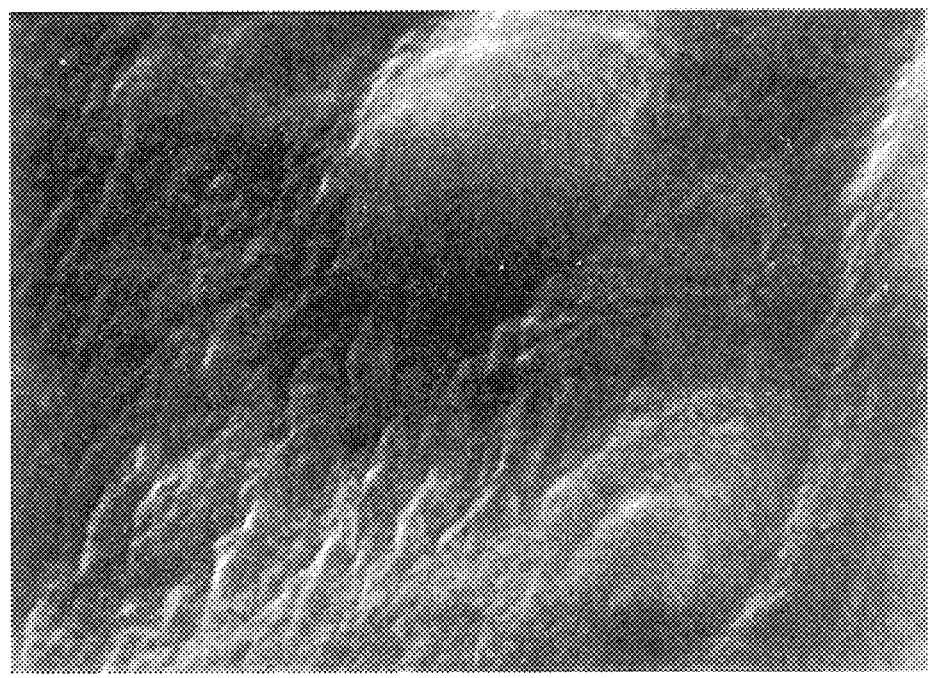

FIGS. 5A and 5B. Scanning electron micrographs of a deacetylated p-GlcNAc mat. Magnification: FIG. 5A: 1000×; FIG. 5B: 10,000×.

Figure 6A:
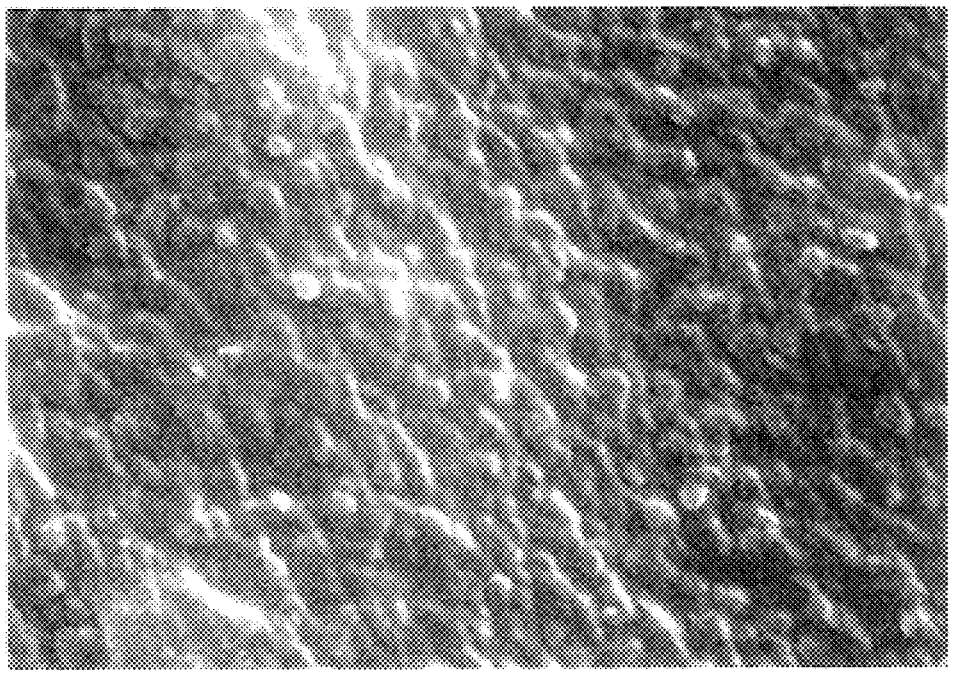
Figure 6B:
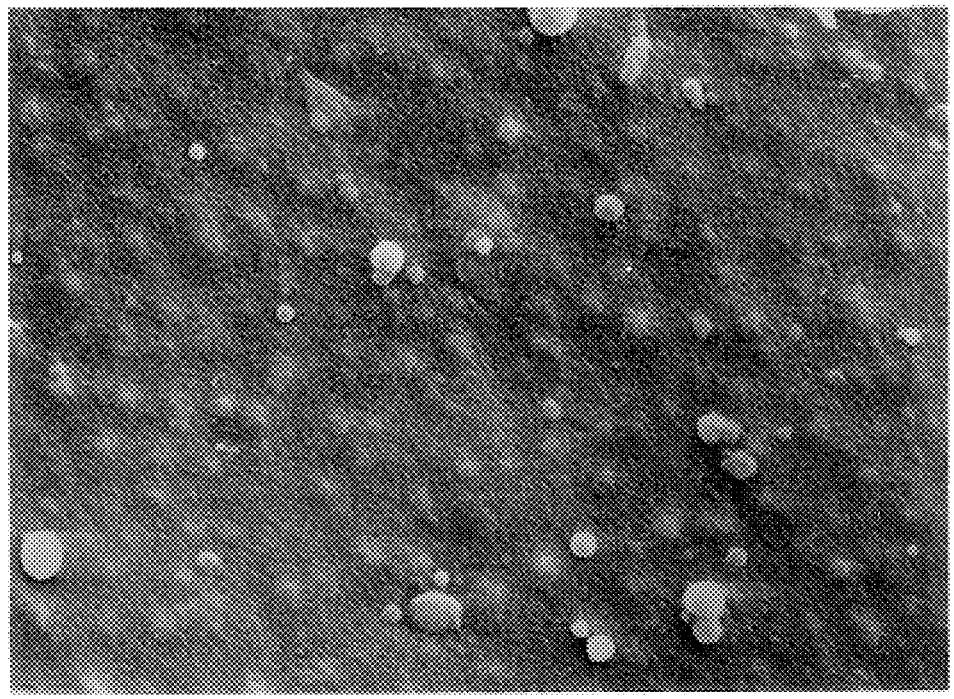

FIGS. 6A and 6B. Scanning electron micrographs of a p-GlcNAc membrane dissolved in dimethylacetamide/lithium chloride and reprecipitated in water into a fibrous material, as described in Example Section 8, infra.

Figure 7:
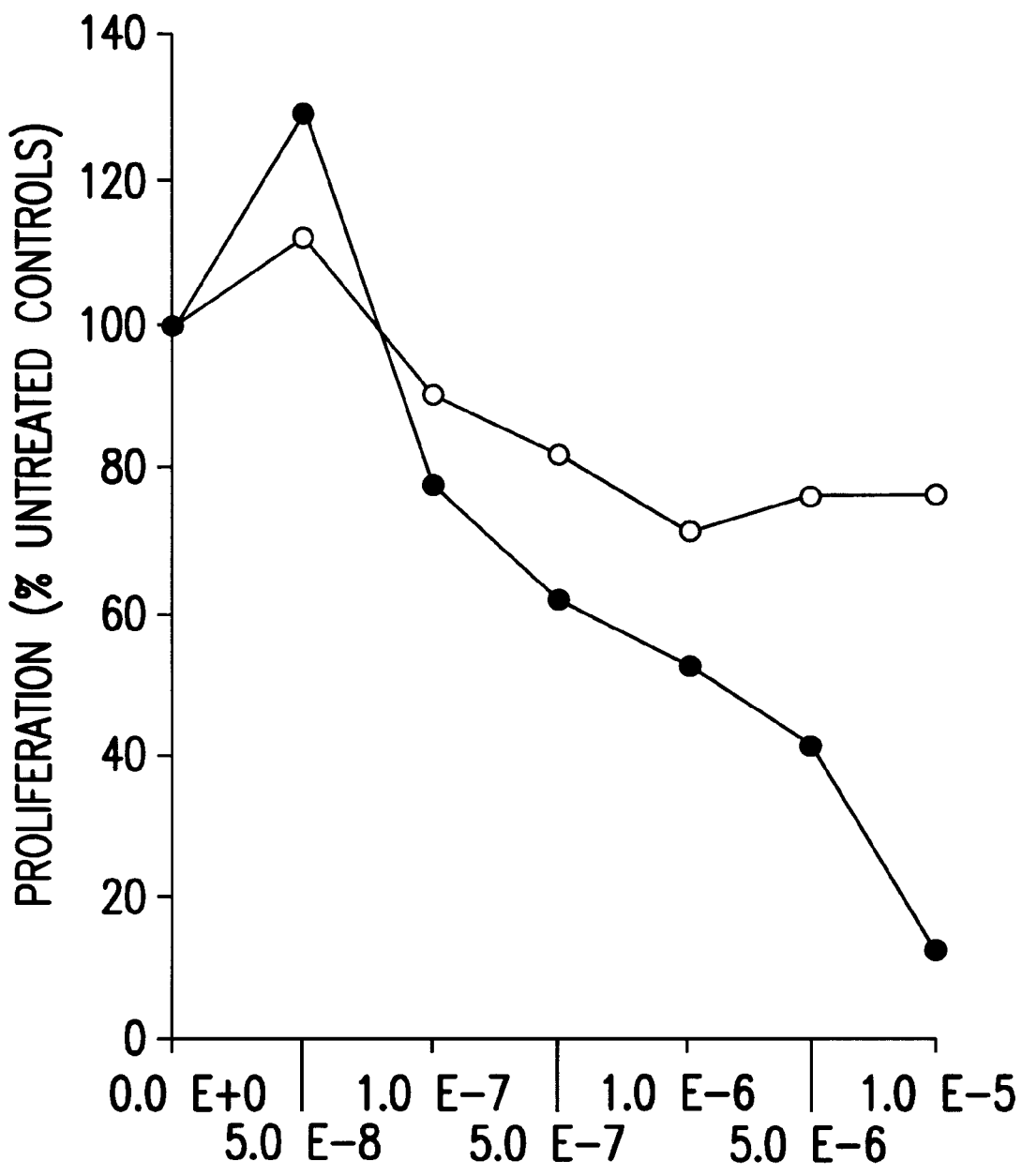

FIG. 7. Endothelin receptor antagonist Ro61 inhibition of B16 melanoma cell proliferation in vitro. Ro61 was added at increasing concentrations to a 96 well culture plate to which B16 cells (closed circles) and splenocytes (open circles) from C57BL/6 (H-2b) mice were then added. Proliferation of the Ro61-treated cells is expressed as a percentage of untreated control cells. Mean values of triplicate wells were determined.

Figure 8:
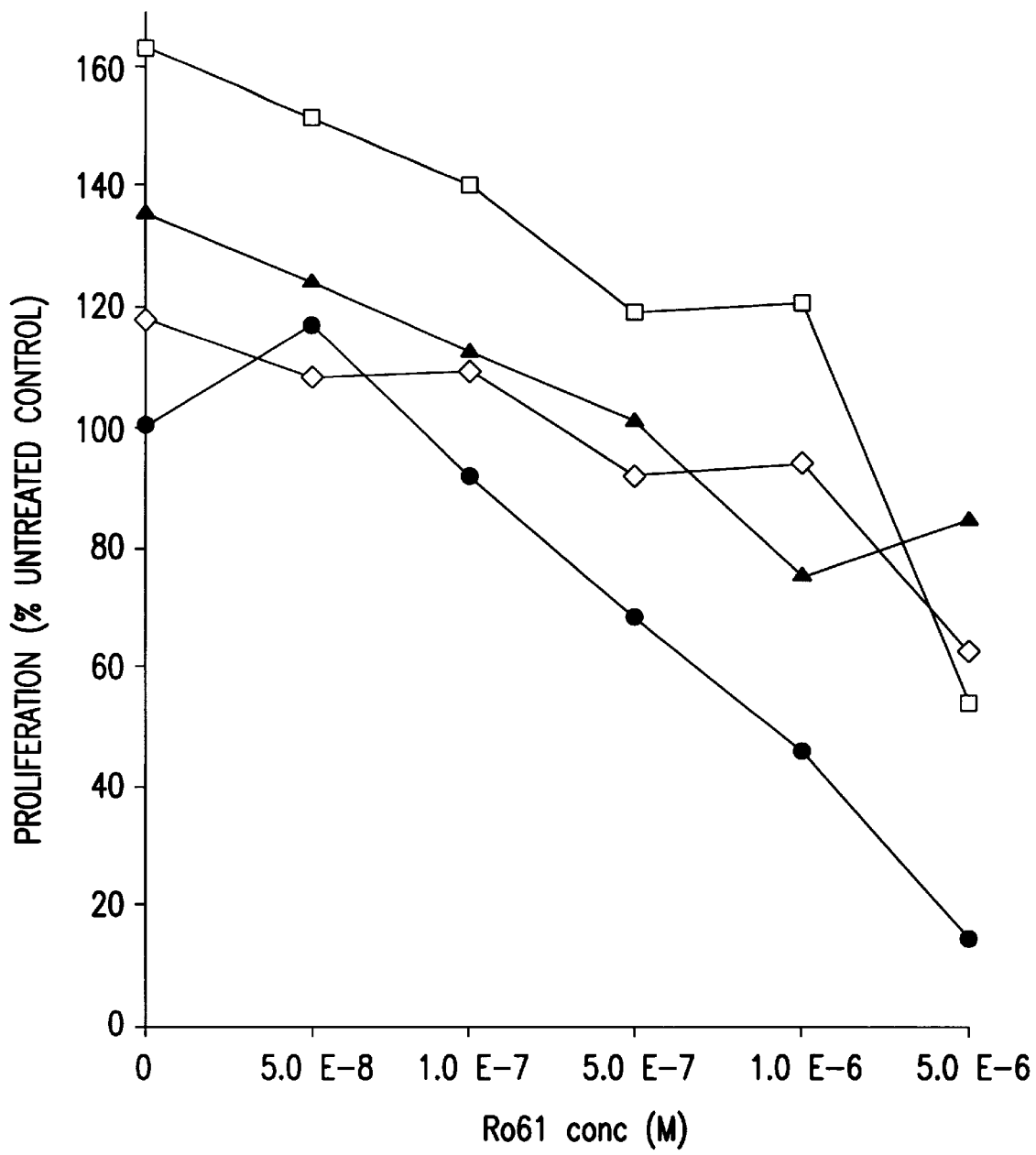

FIG. 8. ETA and ETB agonists reversal of Ro61 inhibition of B16 melanoma cell proliferation in vitro. B16 cells were cultured with either, BQ-3020-[Ac-[Ala11,Ala15]-endothelin(6,21), an ETA agonist (closed triangle), [Ala$^{1,3,11,15}$]-endothelin1, an ETB agonist (open diamond), both ETA and ETB agonists (open box) or neither (closed circle) and Ro61 was then added to each well. Proliferation of the Ro61-treated cells is expressed as a percentage of untreated control cells. Mean values of triplicate wells were determined.

Figure 9:
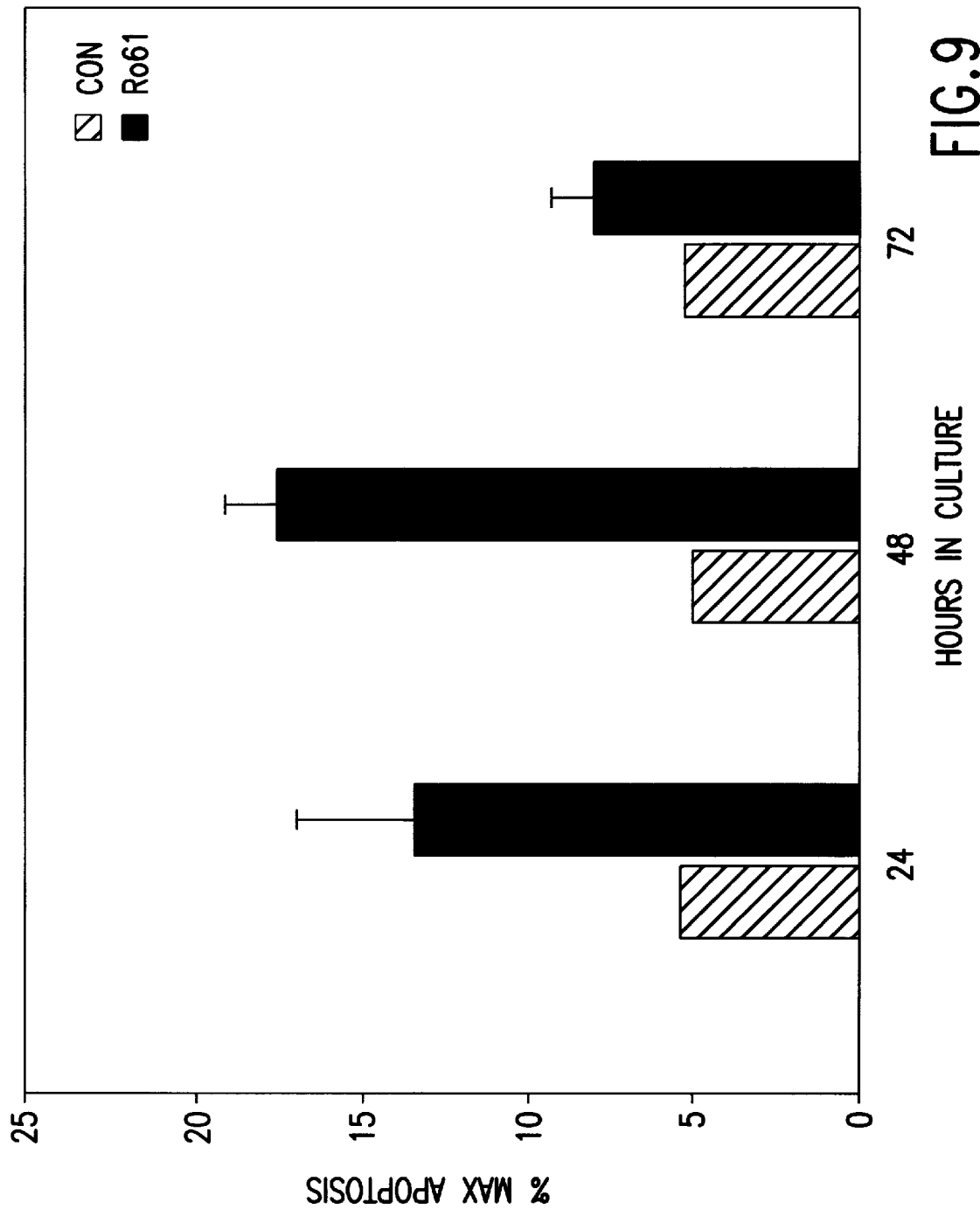

FIG. 9. Ro61 induces apoptosis. B16 cells were assayed for apoptosis with a Fluorescein In Situ Cell Death Detection Kit after being cultured with either common media (Control) or Ro61 (1 μM) (■) for 0, 24, 48, and 72 hours at 37° C.

Figure 10:
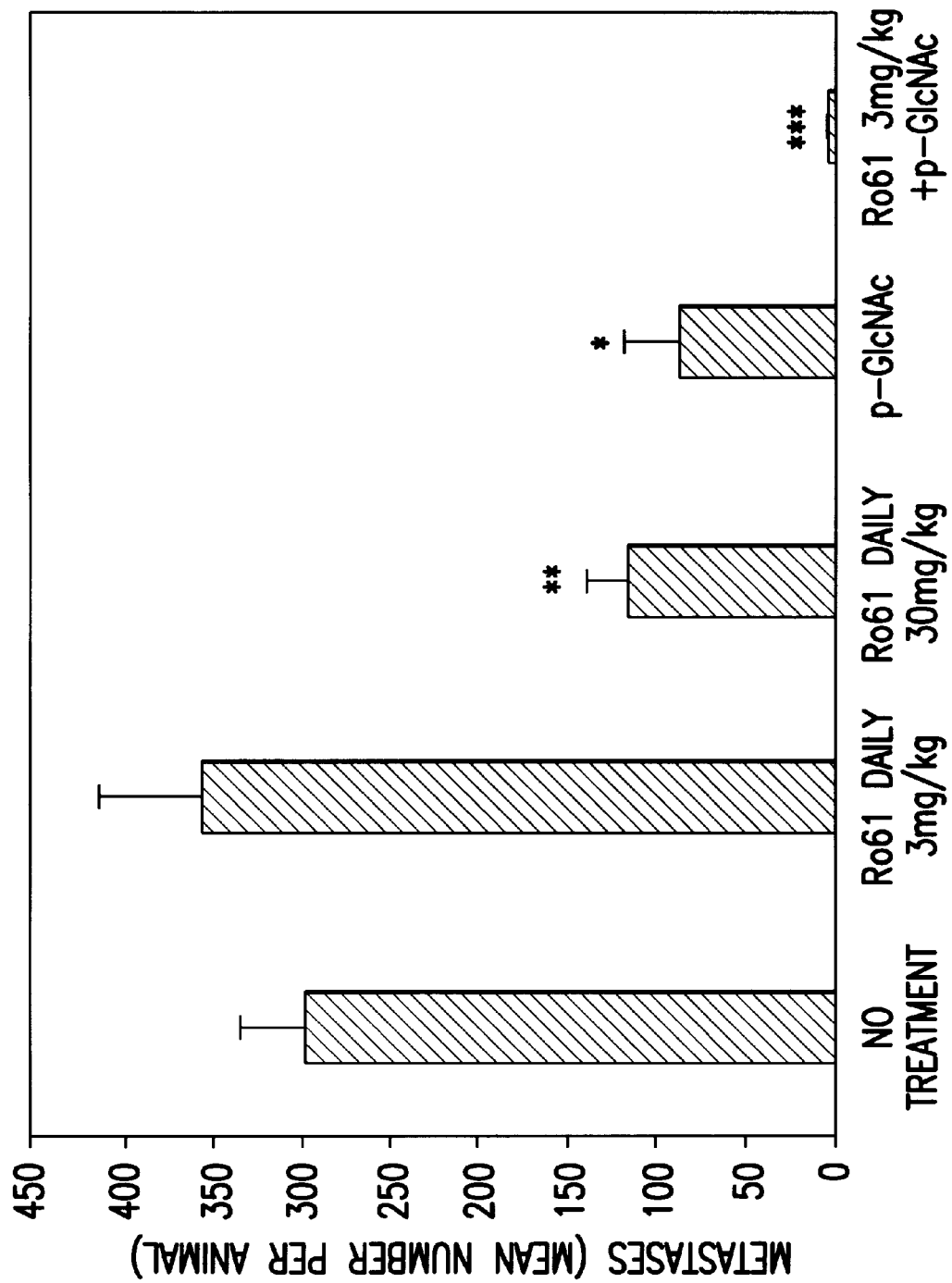

FIG. 10. Ro61 inhibition of B16 melanoma intraperitoneal metastases in vivo. C57BL/6 mice were injected intraperitoneally with B16 cells and one day later, the mice were injected with 100 μl of either HBSS alone (no treatment), HBSS containing 3 mg/kg of Ro61 (administered daily), HBSS containing 30 mg/kg of Ro61 (administered daily), p-GlcNAc gel, and p-GlcNAc gel containing 3 mg/kg of Ro61. Animals were sacrificed after 7 days and evaluated for the presence of intraperitoneal metastatic disease. Values represent the mean number of visible metastases and mean standard error for each group (n=10 or n=13 for no treatment group).

Figure 11:
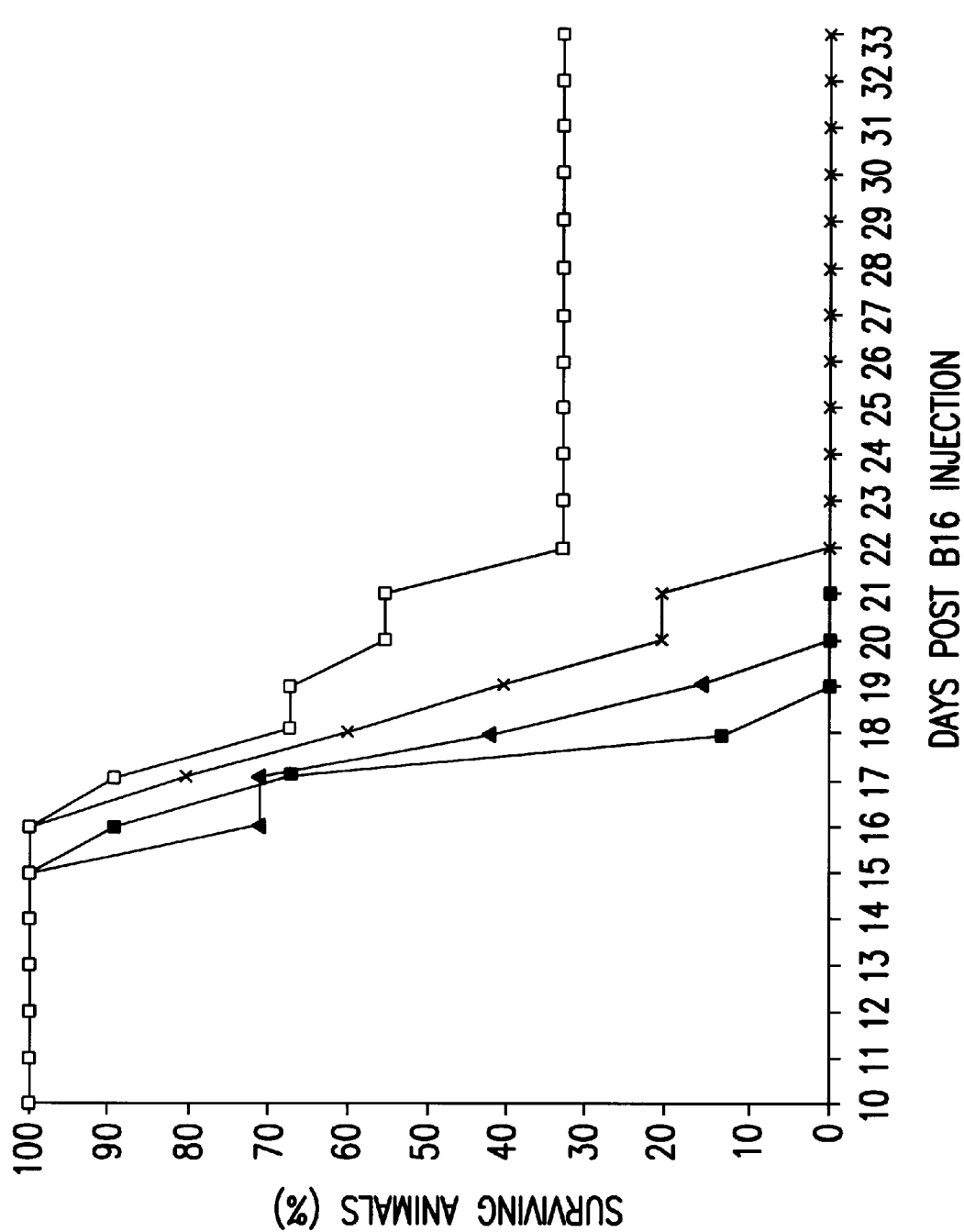

FIG. 11. Long term survival of Ro61-treated C57BL/6 mice after intraperitoneal B16 melanoma challenge. C57BL/6 mice were injected intraperitoneally with B16 cells. Animals were randomly separated into 4 groups for either of the following treatments: (a) no treatment (closed boxes); (b) 100 μl of p-GlcNAc gel alone (crosses); (c) 100 μl of daily HBSS containing 3 mg/kg Ro61 (closed triangles); or (d) 100 μl of p-GlcNAc gel containing 3 mg/kg Ro61 (open boxes). Animals were monitored daily and sacrificed for humane reasons when determined moribund.

Figure 12A:
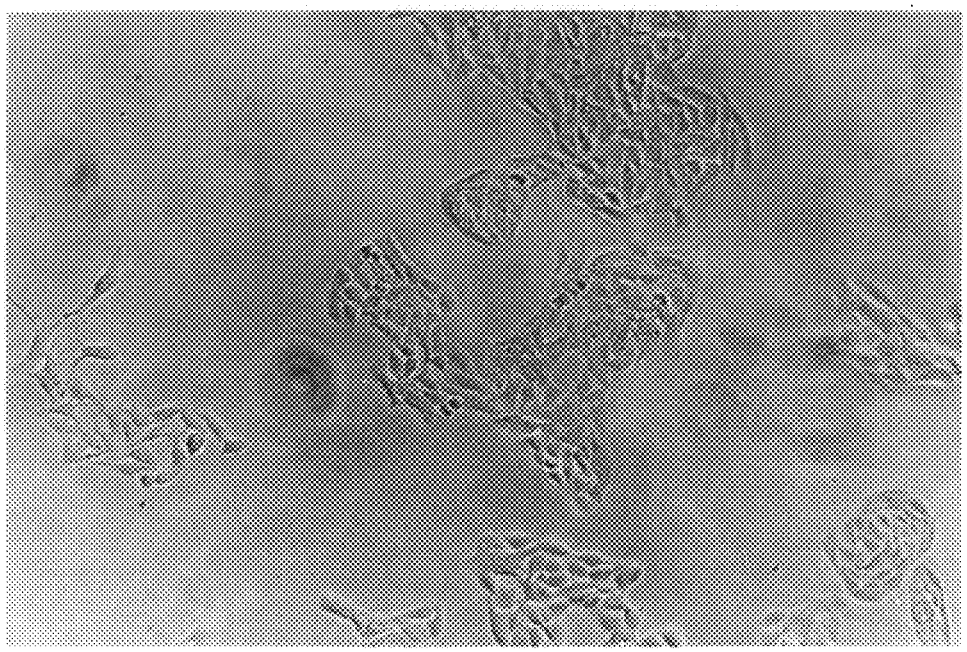
Figure 12B:
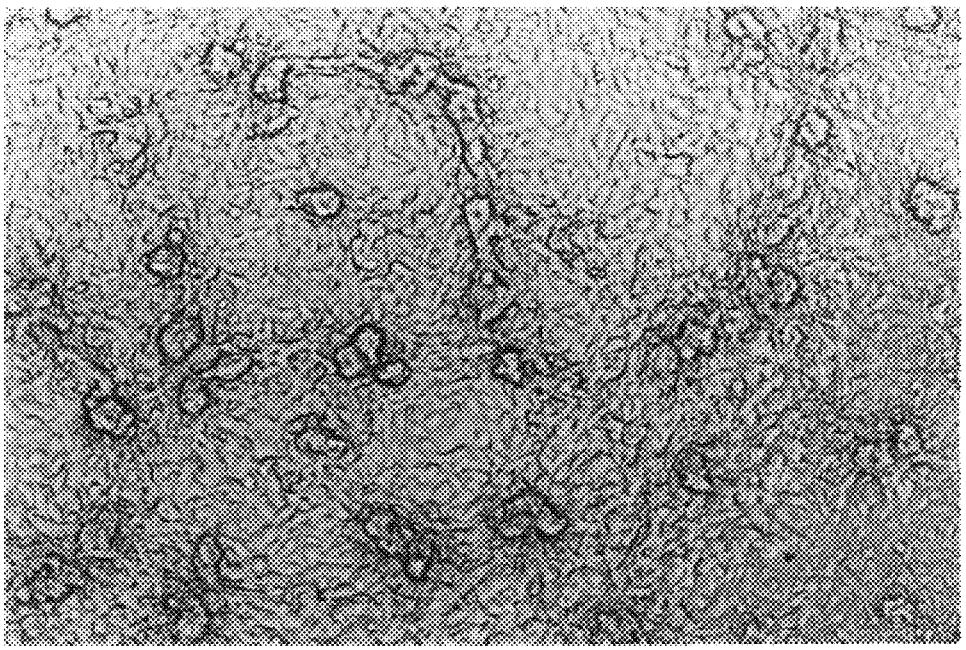

FIGS. 12A and 12B. Photomicrographs of the cell morphology of Ro61-treated (FIG. 12A) and untreated (FIG. 12B) B16 cells at 40× power; $10^{-7}$M Ro61, $10^5$ cells.

5. DETAILED DESCRIPTION OF THE INVENTION

The present invention relates to compositions comprising at least one endothelin antagonist, preferably in combination with a poly-β-1→4-N-acetylglucosamine (p-GlcNAc) polysaccharide matrix, and methods for using these compositions in the treatment of cancer and other proliferative diseases. The endothelin antagonists according to this invention may be specific or non-specific for ETA or ETB receptors or peptide-based or non-peptide-based compounds. According a preferred embodiment of the invention, the endothelin antagonist is a non-peptide-based, non-specific endothelin antagonist. According to another preferred embodiment, the endothelin antagonist is a non-peptide-based pyrimidyl sulfonamide compound, such as the Ro61 compound depicted in FIG. 1 below.

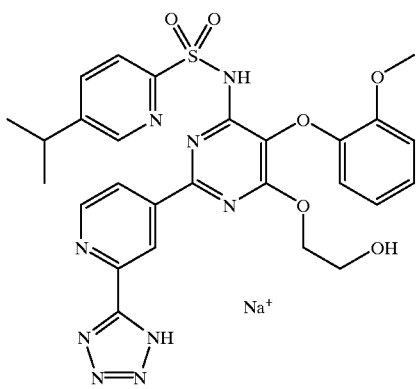

According to the present invention, at least one type of endothelin antagonist, alone or in combination with one or more other antitumor agents, is covalently or non-covalently attached to, or combined with, the p-GlcNAc described in detail in Section 5.1, infra. According to one preferred embodiment of the invention, at least one endothelin antagonist, such as Ro61, is dissolved in a deacetylated p-GlcNAc gel to form an endothelin antagonist ("EA")/p-GlcNAc composition of the invention. According to a further preferred embodiment, the deacetylated p-GlcNAc is derivatized with lactic acid to form a p-GlcNAc-lactate salt.

As defined herein, the term "endothelin antagonist" includes endothelin receptor antagonists and "EA/p-GlcNAc compositions" include compositions wherein at least one type of endothelin antagonist is either covalently attached to the p-GlcNAc or is non-covalently bound to, mixed with or encapsulated within the p-GlcNAc. The compositions of the invention can additionally comprise other antitumor agents, which in combination with the endothelin antagonist, act to inhibit the growth and/or metastasis of tumor or other neoplastic cells. As defined herein, "antitumor agent" includes any compound that inhibits the growth or metastasis of tumor cells, cancer cells, or any other type of neoplastic cell.

This invention is based in part on Applicants' discovery that endothelin antagonists, either alone or in combination with the p-GlcNAc described herein, inhibit the proliferation of neoplastic cells in vitro and decrease metastases and/or increase survival of tumor cell-bearing animals in vivo (See Example Sections 12 through 16, infra). In addition, the p-GlcNAc of this invention alone has an inhibitory effect on metastases and neoplastic cell growth in vivo.

Thus, according to the methods of this invention, pharmaceutical compositions comprising the EA/p-GlcNAc compositions of the invention are administered, in a therapeutically effective amount, to a patient in vivo for the treatment of cancer or other proliferative diseases. Another preferred embodiment of the invention comprises the administration in vivo of an endothelin antagonist, e.g., a pyrimidyl sulfonamide endothelin antagonist for the treatment of proliferative disease. And, yet another embodiment comprises the administration in vivo of the p-GlcNAc described infra for the treatment of proliferative disease.

Solely for ease of description, the detailed description of the invention is divided into the following subsections: (1) The p-GlcNAc of the compositions and methods of the invention; (2) Endothelin antagonists of the compositions and methods of the invention; (3) Preferred formulations of the compositions of the invention; and (4) Uses of the compositions and methods of the invention.

5.1 The p-GlcNAc of the Compositions of the Invention

The p-GlcNAc polysaccharide matrix to be utilized in the compositions and methods of this invention comprises a polymer of high molecular weight ranging from a weight average of about 800,000 daltons to about 30 million daltons, based upon gel permeation chromatography measurements. Such a molecular weight range represents a p-GlcNAc species having about 4,000 to about 150,000 N-acetylglucosamine monosaccharides attached in a β-1→4 configuration, with about 4,000 to about 15,000 N-acetylglucosamine monosaccharides being preferred (FIG. 1).

The variability of the p-GlcNAc is very low, and its purity is very high, both of which are evidenced by chemical and physical criteria. Among these are chemical composition and non-polysaccharide contaminants. First, chemical composition data for the p-GlcNAc produced using two different purification methods is shown in Table I below. As can be seen, the chemical composition of the p-GlcNAc produced by both methods is, within the bounds of experimental error, the same as the formula compositions of p-GlcNAc. Second, as is also shown in Table I, the p-GlcNAc produced is free of detectable protein contaminants, is substantially free of other organic contaminants such as free amino acids, and is substantially free of inorganic contaminants such as ash and metal ions (the p-GlcNAc of the invention may deviate up to about 2% from the theoretical values of carbon, hydrogen, nitrogen and oxygen for pure p-GlcNAc). Therefore, as used herein, the terms "substantially free of organic contaminants" and "substantially free of inorganic contaminants" refer to compositions of p-GlcNAc having the profiles for carbon, hydrogen, nitrogen and oxygen which deviate no more than about 2% from the theoretical values, and preferably, the p-GlcNAc of the invention contain a profile as exemplified in the Experimental Data on p-GlcNAc mats in Table I (allowing for the percent deviation). Further, the p-GlcNAc exhibits a very low percentage of bound water.

TABLE I

CHEMICAL ANALYSIS DATA (% by weight)

Theoretical Values for Pure p-GlcNAc:

| | |
|---|---|
| Carbon | 47.29 |
| Hydrogen | 6.40 |
| Nitrogen | 6.89 |
| Oxygen | 39.41 |
| Protein | 0.00 |

Experimental Data on p-GlcNAc Mats:
(Number of experimental batches for each membrane type being greater than 30 for each membrane type)

| | MECHANICAL FORCE METHOD | | CHEMICAL/BIOLOGICAL METHOD | |
|---|---|---|---|---|
| | Normalized[1] | % Dev. | Normalized[1] | % Dev. |
| Carbon | 47.21 ± 0.08 | −0.17 | 47.31 ± 0.11 | +0.04 |
| Hydrogen | 6.45 ± 0.08 | +0.78 | 6.34 ± 0.08 | −0.94 |
| Nitrogen | 6.97 ± 0.18 | +0.87 | 6.94 ± 0.16 | +0.73 |
| Oxygen | 39.55 ± 0.36 | +0.36 | 39.41 ± 0.10 | 0.00 |
| | Average Values | | Average Values | |
| Protein | 0.00 | | 0.00 | |
| Ash | 1.30 | | 0.98 | |
| Moisture | 2.0 | | 1.2 | |

[1]Raw analytical data have been normalized to account for ash and moisture content of the samples.

The p-GlcNAc of the compositions of the invention exhibits a carbohydrate analysis profile substantially similar to that shown in FIG. 2. The primary monosaccharide of the p-GlcNAc is N-acetylglucosamine. Further, the p-GlcNAc does not contain the monosaccharide glucosamine. Other physical characteristics of the p-GlcNAc are described in detail in U.S. Pat. No. 5,635,493, which has been incorporated herein by reference.

The p-GlcNAc according to this invention exhibits a high degree of biocompatibility, which may be determined by a variety of techniques, including, but not limited to such procedures as the elution test, intramuscular implantation, or intracutaneous or systemic injection into animal subjects. See, e.g., U.S. Pat. No. 5,635,493 incorporated herein by reference.

The p-GlcNAc is produced by, and may be purified from, microalgae, preferably diatoms. The diatoms which may be used as starting sources for the production of the p-GlcNAc include, but are not limited to members of the Coscinodiscus genus, the Cyclotella genus, and the Thalassiosira genus, with the Thalassiosira genus being preferred.

Among the Coscinodiscus genus, the species of diatom that may be used include, but are not limited to the concinnus and radiatus species. The diatoms among the Cyclotella genus which may be used include, but are not limited to the caspia, cryptica, and meneghiniana species. The Thalassiosira diatoms that may be utilized to produce the starting material for the p-GlcNAc of this invention include, but are not limited to the nitzschoides, aestivalis, antarctica, deciphens, eccentrica, floridana, fluviatilis, gravida, guillardii, hyalina, minima, nordenskioldii, oceanica, polychorda, pseudonana; rotula, tubifera, tumida, and weissflogii species, with the fluviatilis and weissflogii species being preferred. Diatoms such as those described above may be obtained, for example, from the culture collection of the Bigelow Laboratory for Ocean Sciences, Center for Collection of Marine Phytoplankton (McKown Point, West Boothbay Harbor, Me., 04575). Any of these diatoms may be grown utilizing the methods and nutrient medium described in U.S. Pat. No. 5,635,493 incorporated herein by reference.

p-GlcNAc fibers may be obtained from diatom cultures such as those described above via a number of different methods. According to the Mechanical Force method, p-GlcNAc fibers may be separated from diatom cell bodies by subjecting the contents of the culture to an appropriate mechanical force. Such a mechanical force may include, but is not limited to, a shear force generated by, for example, a colloid mill, an ultrasound device, or a bubble generator, or a cutting force generated by, for example, a Waring blender.

The resulting suspension of diatom cell bodies and p-GlcNAc fibers are then segregated. For example, the suspension may be subjected to a series of centrifugation steps which segregate the p-GlcNAc fibers from the cell bodies, yielding a clear supernatant exhibiting little, if any, visible flocculent material. A fixed angle rotor, and a temperature of about 10° C. are preferred for the centrifugation steps. The speed, duration, and total number of centrifugation steps required may vary depending on, for example, the specific centrifugation rotor being used, but the determination of the values for such parameters will be apparent to one of ordinary skill in the art.

The p-GlcNAc fibers in the supernatant may then be concentrated using techniques well known to those of skill in the art. Such techniques may include, but are not limited to suction and filtration devices. Finally, the concentrated p-GlcNAc fibers are washed with, for example, distilled-deionized water, HCl and ethanol, or other appropriate solvents, preferably solvents, such as alcohols, in which both organic and inorganic materials dissolve. An example demonstrating the use of this method for the purification of p-GlcNAc is set forth in Example Section 6, infra.

According to the Chemical/Biological Method, p-GlcNAc fibers are separated from diatom cell bodies by subjecting them to chemical and/or biological agents. For example, diatom cultures may be treated with a chemical capable of weakening diatom cell walls, which leads to a release of the p-GlcNAc fibers without altering their structure. Such a chemical may include, but is not limited to, hydrofluoric acid (HF). Alternatively, a mature diatom culture may be treated with a biological agent capable of altering a biological process and may be used to inhibit p-GlcNAc fiber synthesis, thus releasing the fibers already present. For example, such an agent may include, but is not limited to, polyoxin-D, an inhibitor of the enzyme N-acetylglucosaminyl-P-transferase.

The cell bodies and p-GlcNAc-containing fibers of diatom cultures treated with a member of the above described chemical or biological agents are then segregated. For example, the contents of treated diatom cultures may be allowed to settle such that the contents of the cultures are allowed to form two distinct layers. The upper layer will contain primarily the p-GlcNAc fibers, while the bottom layer will contain the cell bodies. The upper p-GlcNAc fiber-containing layer may be siphoned off, leaving behind the settled cellular material of the bottom layer. The siphoned off p-GlcNAc fiber-containing layer may then be further purified to remove protein and other unwanted matter by treatment with a detergent that will not damage the p-GlcNAc fibers. Such a detergent may include, but is not limited to, sodium dodecyl sulfate (SDS).

When acid treatment, such as HF treatment, is used to separate p-GlcNAc fibers from diatom cell bodies, a step may be included for the dispersal of the fibers. Such a step may include, but is not limited to, the use of mechanical force for fiber dispersal, such as a step in which the fibers are subjected to the movements of an orbital shaker.

Alternatively, the acid-treated suspension may, in an optional step, be neutralized prior to further purification by detergent treatment. Such neutralization will, in general, change the pH of the suspension from approximately 1.8 to approximately 7.0, and may be accomplished by, for example, the addition of an appropriate volume of 1M Tris (pH 8.0) or the addition of an appropriate volume of sodium hydroxide (NaOH). Neutralization, in general, yields pure p-GlcNAc fibers of a substantially greater length than the other purification methods discussed herein.

The purified p-GlcNAc fibers may then be concentrated using techniques well known to those of skill in the art, such as by utilizing a suction and filtration device. Finally, the p-GlcNAc fibers are washed, in a series of steps with distilled-deionized water, HCl and ethanol, or other appropriate solvents, preferably solvents, such as alcohols, in which both organic and inorganic materials dissolve. An example demonstrating the successful utilization of such a purification method is set forth in Example Section 7, infra.

While each of these methods for the purification of p-GlcNAc from microalgae, preferably diatom, starting sources produces very pure, unadulterated, crystalline p-GlcNAc, each of the methods yields p-GlcNAc having specific characteristics and advantageous features. For example, the p-GlcNAc purified via the Mechanical Force method produces a p-GlcNAc membrane that provides a superior substrate for the attachment of cells to the p-GlcNAc. The Chemical/Biological method produces a much higher average yield than the average p-GlcNAc yield produced by the Mechanical Force method. Additionally, the acid treatment/neutralization variation of the Chemical/Biological method produces extremely long p-GlcNAc fibers, with some fibers being in excess of 100 μm, and containing molecules of the p-GlcNAc polymer of very high molecular weight, as high as 20–30 million daltons.

The electron micrographic structure of the p-GlcNAc to be utilized in the compositions and methods of this invention, produced using the acid treatment/neutralization variation of the chemical/biological purification method is depicted in FIG. 3. Purification of the p-GlcNAc fibers often results in the formation of fibrous membranes as depicted in FIG. 3.

5.1.1 Derivatization of p-GlcNAc

The fully acetylated p-GlcNAc of the invention may be derivatized, by utilizing a variety of controlled conditions and procedures, into a large range of different compounds. See FIG. 4 for a diagram depicting some of these compounds. Such derivatized compounds may include, but are not limited to, partially or completely deacetylated p-GlcNAc, which has been modified via chemical and/or enzymatic means as described in further detail below. According to a preferred embodiment of the invention, the p-GlcNAc is a 100% deacetylated p-GlcNAc.

Additionally, p-GlcNAc, or its deacetylated derivative, may be derivatized by being sulfated, phosphorylated, and/or nitrated. Further, as detailed below, O-sulfonyl, N-acyl, O-alkyl, N-alkyl, deoxyhalogen, and N-alkylidene and N-arylidene and other derivatives may be prepared from the p-GlcNAc or deacetylated p-GlcNAc of the invention. The deacetylated p-GlcNAc of the invention may also be used to prepare a variety of organic salts and/or metal chelates.

According to a preferred embodiment of the invention, one or more of the monosaccharide units of the p-GlcNAc may be deacetylated to form a deacylated poly-β-1→4-N-glucosamine species. A poly-β-1→4-N-glucosamine species in which each of the monosaccharide units of the poly-β-1→4-N-acetylglucosamine species has been deacetylated, i.e., a 100% deacetylated derivative, will have a molecular weight of about 640,000 daltons to about 24 million daltons, with about 640,000 daltons to about 2.4 million daltons being preferred. A species with such a molecular weight range represents a species having about 4000 to about 150,000 glucosamine monosaccharides covalently attached in a β-1→4 configuration.

The p-GlcNAc may be deacetylated by treatment with a base to yield glucosamines with free amino groups. This hydrolysis process may be carried out with solutions of concentrated sodium hydroxide or potassium hydroxide at elevated temperatures. See, e.g., Example Section 8, infra. Alternatively, an enzymatic procedure utilizing a chitin deacetylase enzyme may be used for p-GlcNAc deacylation. Such a deacetylase enzymatic procedure is well known to those of skill in the art and may be performed as in U.S. Pat. No. 5,219,749, which is incorporated herein, by reference, in its entirety.

Further, one or more of the monosaccharide units of the p-GlcNAc of the invention may be derivatized to contain at least one sulfate group, or, alternatively, may be phosphorylated or nitrated, as depicted below:

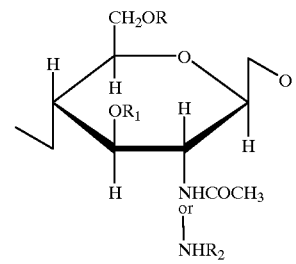

where, R and/or $R_1$, in place of a hydrogen, and/or $R_2$, in place of —COCH$_3$, may be a sulfate (—SHO$_3$), a phosphate (—P(OH)$_2$), or a nitrate (—NO$_2$) group.

Described below are methods by which such p-GlcNAc derivatives may be prepared. Before performing these methods, it may be advantageous to first lyophilize, freeze in liquid nitrogen, and pulverize the p-GlcNAc starting material.

Sulphated p-GlcNAc derivatives may be generated, by, for example, a two step process. In the first step, O-carboxymethyl p-GlcNAc may be prepared from the p-GlcNAc and/or p-GlcNAc derivatives of the invention by, for example, utilizing techniques such as those described by Tokura et al. (Tokura, S. et al., 1983, Polym. J. 15:485).

Second, the sulfation step may be carried out with, for example, N,N-dimethyl-formamide-sulfur trioxide, according to techniques well known to those of skill in the art, such as are described by Schweiger (Schweiger, R. G., 1972, Carbohydrate Res. 21:219). The resulting product may be isolated as a sodium salt.

Phosphorylated p-GlcNAc derivatives may be prepared, for example, by utilizing techniques well known to those of skill in the art, such as those described by Nishi et al. (Nishi, N. et al., 1986, in "Chitin in Nature and Technology, Muzzarelli et al., eds. Plenum Press, New York, pp. 297–299). Briefly, a p-GlcNAc/methanesulfonic acid mixture may be treated with phosphorus pentoxide (in an approximately 0.5 to 4.0 molar equivalent) with stirring, at a temperature of about 0° C. to about 5° C. Treatment may be for about 2 hours. The resulting product may then be precipitated and washed using standard techniques well known to those of skill in the art. For example, the sample may be precipitated with a solvent such as ether, centrifuged, washed with a solvent such as ether, acetone, or methanol, and dried.

Nitrated p-GlcNAc derivatives may be prepared by utilizing techniques well known to those of skill in the art, such as those described by Schorigin and Halt (Schorigin, R. and Halt, E., 1934, Chem. Ber. 67:1712). Briefly, p-GlcNAc and/or a p-GlcNAc derivative may be treated with concentrated nitric acid to form a stable nitrated product.

One or more of the monosaccharide units of the p-GlcNAc of the invention may contain a sulfonyl group, as depicted below:

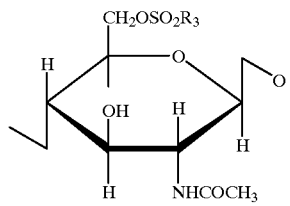

where $R_3$ may be an alkyl, an aryl, an alkenyl, or an alkynyl moiety. Such a derivative may be generated by well known methods such as the method described in Kurita et al. (Kurita, K. et al., 1990, Polym. Prep [Am. Chem. Soc., Div. Polym. Chem.] 31:624–625). Briefly, an aqueous alkali p-GlcNAc solution may be reacted with a chloroform solution of tosyl chloride, and the reaction may then be allowed to proceed smoothly at low temperatures.

One or more of the monosaccharides of the p-GlcNAc of the invention or its deacetylated derivative may contain one or more O-acyl groups, as depicted below:

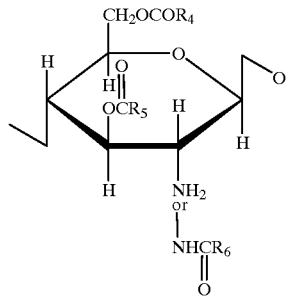

where $R_4$ and/or $R_5$, in place of hydrogen, may be an alkyl, an alkenyl, or an alkynyl moiety, and $R_6$ may be an alkyl, an alkenyl, or an alkynyl moiety. An example of such a derivative may be generated by well known methods such as those described by Komai (Komai, T. et al., 1986, in "Chitin in Nature and Technology", Muzzarelli et al., eds., Plenum Press, New York, pp. 497–506). Briefly, p-GlcNAc may be reacted with any of a number of suitable acyl chlorides in methanesulfonic acid to yield p-GlcNAc derivatives which include, but are not limited to, caproyl, capryl, lanoyl, or benzoyl derivatives.

One or more of the monosaccharides of the deacetylated p-GlcNAc of the invention may contain an N-acyl group, as depicted below:

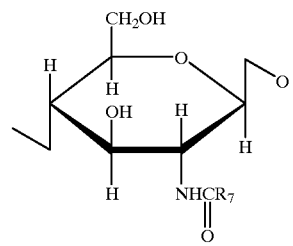

where $R_7$ may be an alkyl, an alkenyl, or an alkynyl moiety. Such a derivatization may be obtained by utilizing techniques well known to those of skill in the art, such as the technique described in Hirano et al. (Hirano, S. et al., 1976, Carbohydrate Research 47:315–320). Deacetylated p-GlcNAc is soluble in a number of aqueous solutions of organic acids. The addition of selected carboxylic anhydrides to such p-GlcNAc-containing solutions, in aqueous methanolic acetic acid, results in the formation of N-acyl p-GlcNAc derivatives. N-acyl p-GlcNAc is a preferred derivative for the production of controlled release drug delivery systems.

One or more of the monosaccharides of the p-GlcNAc of the invention or of its deacetylated derivative, may contain an O-alkyl group, as depicted below:

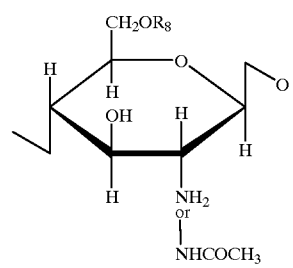

where $R_8$ may be an alkyl, and alkenyl, or a alkynyl moiety. Such a derivatization may be obtained by using techniques well known to those of skill in the art. For example, the procedure described by Maresh et al. (Maresh, G. et al., in "Chitin and Chitosan," Skjak-Braek, G. et al., eds., 1989, Elsevier Publishing Co., pp. 389–395). Briefly, deacetylated p-GlcNAc may be dispersed in dimethoxyethane (DME) and reacted with an excess of propylene oxide. The period of the reaction may be 24 hours, and the reaction takes place in an autoclave at 40 to 90° C. The mixture may then be diluted with water and filtered. The DME may be removed by distillation. Finally, the end-product may be isolated via lyophilization. The O-alkyl p-GlcNAc and its deacetylated derivative is also a preferred derivative for the production of controlled release drug delivery systems.

One or more of the monosaccharide units of the p-GlcNAc of the invention may be an alkali derivative, as depicted below:

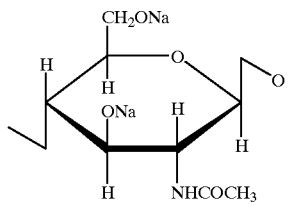

Such a derivative may be obtained by using techniques well known to those of skill in the art. For example, a method such as that described by Noguchi et al. (Noguchi, J. et al., 1969, Kogyo Kagaku Zasshi 72:796–799) may be utilized. Briefly, p-GlcNAc may be steeped, under vacuo, in NaOH (43%, preferably) for a period of approximately two hours at about 0° C. Excess NaOH may then be removed by, for example, centrifugation in a basket centrifuge and by mechanical pressing.

One or more of the monosaccharide units of the deacetylated derivative of the p-GlcNAc of the invention may contain an N-alkyl group, as depicted below:

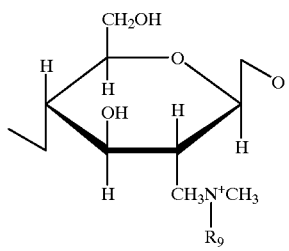

where $R_9$ may be an alkyl, an alkenyl, or an alkynyl moiety. Such a derivatization may be obtained by utilizing, for example, a procedure such as that of Maresh et al. (Maresh, G. et al., in "Chitin and Chitosan," Skjak-Brack, G. et al., eds. 1989, Elsevier Publishing Co., pp. 389–395), as described, above, for the production of N-alkyl p-GlcNAc derivatives.

One or more of the monosaccharide units of the deacetylated derivative of the p-GlcNAc of the invention may contain at least one deoxyhalogen derivative, as depicted below:

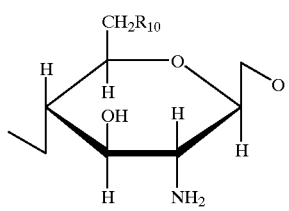

where $R_{10}$ may be F, Cl, Br, or I, with I being preferred. Such a derivative may be obtained by using techniques well known to those of skill in the art. For example, a procedure such as that described by Kurita et al. (Kurita, K. et al., 1990, Polym. Prep. [Am. Chem. Soc. Div. Polym. Chem.] 31:624–625) may be utilized. Briefly, a tosylated p-GlcNAc is made to react with a sodium halide in dimethylsulfoxide, yielding a deoxyhalogen derivative. p-GlcNAc tosylation may be performed by reacting an aqueous alkali p-GlcNAc solution with a chloroform solution of tosyl chloride. Such a reaction may proceed smoothly at low temperatures.

One or more of the monosaccharide units of the deacetylated derivative of the p-GlcNAc of the invention may form a salt, as depicted below:

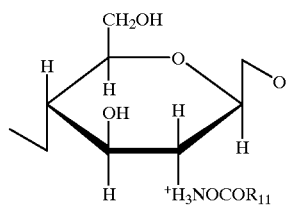

where $R_{11}$ may be an alkyl, an alkenyl, or an alkynyl moiety. Such a derivatization may be obtained by using techniques well known to those of skill in the art. For example, a procedure such as that described by Austin and Sennett (Austin, P. R. and Sennett, S., in "Chitin in Nature and Technology," 1986, Muzzarelli, R. A. A. et al., eds. Plenum Press, pp. 279–286) may be utilized. Briefly, deacetylated p-GlcNAc may be suspended in an organic medium such as, for example, ethyl acetate or isopropanol, to which may be added an appropriate organic acid such as, for example, formic, acetic, glycolic, or lactic acid. The mixture may be allowed to stand for a period of time (1 to 3 hours, for example). The temperature of reaction and drying may vary from about 12° to about 35° C., with 20° to 25° C. being preferred. The salts may then be separated by filtration, washed with fresh medium, and the residual medium evaporated.

One or more of the monosaccharide units of the deacetylated derivative of the p-GlcNAc of the invention may form a metal chelate, as depicted below:

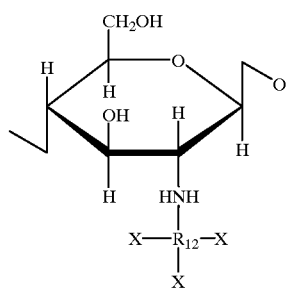

where $R_{12}$ may be a metal ion, particularly one of the transition metals, and X is the dative bond established by the nitrogen electrons present in the amino and substituted amino groups present in the deacetylated p-GlcNAc.

One or more of the monosaccharide units of the deacetylated derivative of the p-GlcNAc of the invention may contain an N-alkylidene or an N-arylidene group, as depicted below:

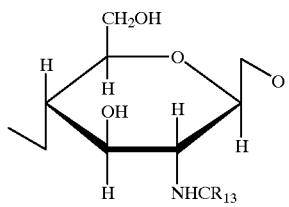

where $R_{13}$ may be an alkyl, an alkenyl, an alkynyl, or an aryl moiety. Such a derivatization may be obtained by using techniques well known to those of skill in the art. For example, a procedure such as that described by Hirano et al. (Hirano, S. et al., 1981, J. Biomed. Mat. Res. 15:903–911) may be utilized. Briefly, an N-substitution reaction of deacetylated p-GlcNAc may be performed with carboxylic anhydrides and/or arylaldehydes to yield acyl- and/or arylidene derivatives.

Further, the p-GlcNAc, or its deacetylated derivative, may be subjected to controlled hydrolysis conditions, which yield groups of molecules having uniform, discrete molecular weight and other physical characteristics. Such hydrolysis conditions may include, for example, treatment with the enzyme, lysozyme. p-GlcNAc may be exposed to lysozyme for varying periods of time, in order to control the extent of hydrolysis. In addition, the rate of hydrolysis may be controlled as a function of the extent to which the p-GlcNAc that is being lysozyme-treated has been deacetylated. Deacetylation conditions may be as described supra. The more fully a p-GlcNAc molecule has been deacetylated, between about 20 and about 90 percent deacetylated, the more fully the molecule will be hydrolyzed in a given time. Changes in physical characteristics, in addition to the lowering of molecular weight, may be elicited by hydrolysis and/or deacetylation treatments. Extensive hydrolysis causes liquefication of the p-GlcNAc.

Further, heat denaturation may function to modify the crystalline structure of the p-GlcNAc. Such a modification of the p-GlcNAc product crystalline structure may advantageously affect, for example, the reactivity of the p-GlcNAc.

In addition, hybrids comprising p-GlcNAc and/or p-GlcNAc derivatives may be formed. Such hybrids may contain any of a number of natural and/or synthetic materials, in addition to p-GlcNAc and/or p-GlcNAc derivatives. For example, hybrids may be formed of p-GlcNAc and/or p-GlcNAc derivatives plus one or more extracellular matrix (ECM) components. Such ECM components may include, but are not limited to, collagen, fibronectin, glycosaminoglycans, and/or peptidoglycans. Hybrids may also be formed of p-GlcNAc and/or p-GlcNAc derivatives plus one or more synthetic materials such as, for example, polyethylene. Such a p-GlcNAc/polyethylene or p-GlcNAc derivative/polyethylene hybrid may be made by thermally linking the hybrid components via, for example, autoclaving.

Preferred p-GlcNAc derivatives for use in the claimed invention are deacetylated p-GlcNAc salt derivatives such as a p-GlcNAc-lactate derivative, especially a p-GlcNAc-lactate gel derivative. As used herein, the term "p-GlcNAc-lactate" means that the lactic acid moiety is functionally attached to a partially or fully deacetylated p-GlcNAc. Such p-GlcNAc-lactate derivatives may be obtained as described above (e.g., by derivatization with lactic acid) and formulated as a gel using propylene glycol and water, as described in Example Section 10, infra. p-GlcNAc-lactate derivatives may be produced having high and low viscosities, which allows for the ability to tailor the p-GlcNAc to the specific indication of interest. For example, it may be useful to use a p-GlcNAc having a lower viscosity for delivery through a syringe or via a spray.

As described in greater detail in Section 5.3, infra, the p-GlcNAc and/or its derivatives as described above, can be further derivatized by the covalent or non-covalent attachment to, or combination with, molecules or drugs of interest such as endothelin antagonists.

5.1.2 Reformulations of p-GlcNAc

The p-GlcNAc, its deacetylated derivatives and/or their derivatizations, such as those described above, to be used in the compositions of the invention, may be dissolved and subsequently reformulated into a variety of shapes and configurations.

Solution of the p-GlcNAc can be achieved by treatment with dimethyl acetamide (DMA)/lithium chloride. p-GlcNAc may be readily dissolved by stirring in a DMA solution containing 5% LiCl (by weight of the DMA). Water-soluble p-GlcNAc derivatives, such as p-GlcNAc salts, e.g., lactate or carboxymethyl derivatives, may be dissolved in water. p-GlcNAc which has been at least about 75% deacetylated may be put into solution in, for example, a mild acidic solution, such as 1% acetic acid. p-GlcNAc derivatives that are water-insoluble may be put into solution in organic solvents.

Derivatization of p-GlcNAc in DMA:LiCl with phenyl isocyanates may be used to produce carbanilates. Further, derivatization of p-GlcNAc in DMA:LiCl with toluene-p-sulphonylchloride may be used to produce toluene-p-sulfonate.

The p-GlcNAc, its deacetylated derivatives, and/or their derivatizations in solution may then be precipitated and reformulated into shapes which include, but are not limited to, mats, strings, microspheres, microbeads, membranes, fibers, powders, sponges and gels. Further, ultrathin (i.e., less than about 1 micron thick) uniform membranes may be formulated. Additionally, pharmaceutical formulations such as pills, tablets and capsules can be prepared.

Such reformulations may be achieved, by, for example, taking advantage of the fact that pure p-GlcNAc is insoluble in solutions such as water and alcohol, preferably ethanol. Introduction, by conventional means, such as by injection, for example, of the p-GlcNAc-containing DMA/LiCl mixture into such a water or alcohol, preferably ethanol, solution will bring about the reprecipitation, and therefore reformulation, of the dissolved p-GlcNAc. The reformulation of a p-GlcNAc membrane into a fibrous material is demonstrated in Example Section 9, infra. In the case of water-soluble p-GlcNAc derivatives, reformulations may be achieved by reprecipitating in such organic solvents as, for example, ethyl acetate or isopropanol. Reformulations of p-GlcNAc which has been at least about 75% deacetylated may be achieved by reprecipitating in an alkaline solution. Water-insoluble p-GlcNAc derivatives may be reformulated by reprecipitation in aqueous solutions, such as, for example, water.

p-GlcNAc membranes and three-dimensional p-GlcNAc matrices may be produced via methods which provide for the formation of controlled average pore sizes within either the membranes or the matrices. Pore size can be controlled in membranes and matrices by varying the amount of p-GlcNAc material used, and by the addition of certain solvents such as methanol or ethanol, with ethanol being preferred, in specific amounts, ranging from about 5% to about 40%, prior to the formation of membranes and/or matrices. In general, the greater the percentage of solvent, the smaller the average pore size formed will be.

According to a preferred reformulation of the invention, a p-GlcNAc lactate derivative is formulated into a gel as described in detail in Example Section 10, infra.

5.2 The Endothelin Antagonists of the Compositions of the Invention

The endothelin antagonists to be utilized in the compositions and methods of the invention include but are not limited to peptide-based endothelin antagonists, non-peptide-based endothelin antagonists, ETA-specific, ETB-specific, or non-specific endothelin antagonists. Examples of peptide-based endothelin receptor antagonists useful in the compositions and methods of the invention include BQ-123 (Cyclo(-D-Trp-D-Asp-L-Pro-D-Val-L-Leu-), BQ-153, BQ-238, BQ-485, BQ-610, BQ-788, BQ-928, TAK-044, FR139317 (Perhydroazepin-1-ylcarbonyl-L-leucyl-(1-methyl)-D-tryptophyl-[3-(2-pyridyl)]-D-alanine), RES-701-1, PD 142893 (Acetyl-(3,3-diphenyl-D-alanine)-L-Leu-L-Asp-L-Ile-L-Ile-L-Trp), PD 145065, CP 170687, Ac-DBhg16-Leu-Asp-Ile and ET-1[Dprl-Asp 15].

Examples of non-peptide-based endothelin receptor antagonists for use in the compositions and methods of the invention include Ro 61-0612, Ro 61-1790, Ro 42-2005, Ro 46-2005, Ro 46-8443, Ro 47-0203 (also known in the art as bosentan), PD 155080, PD 156707, SB 209670, SB 217242, L-744,453, L-749,329, L-754,142, CGS 27830, BMS 182874, LU 135252, S-1039, mA386, A-127722, TBC11251, Nz-arg-3-(isoxazdylsulfameyl)-2-thiophenecarboxamide, and EQ 123. See, e.g., Webb et al., supra and Ohlstein et al., supra, for structures of many of these known endothelin antagonists.

Non-peptide-based endothelin antagonists may be preferred according to this invention because they display more favorable pharmacokinetic properties than peptide-based antagonists, e.g., enhanced metabolic stability and better bioavailability and oral activity. According to a preferred embodiment of the invention, the endothelin antagonist utilized is Ro61 as depicted in FIG. I, supra.

5.3 Preferred Formulations of the Compositions of the Invention

According to a preferred embodiment of the invention, an endothelin antagonist as described supra ("EA") is covalently or non-covalently functionally attached to, or combined with, the p-GlcNAc, or one or more derivatives or reformulations thereof, as described supra. According to one embodiment, at least one type of endothelin antagonist is covalently, non-covalently or otherwise combined or mixed with a deacetylated p-GlcNAc. Other antitumor agents which may be used in conjunction with the EA/p-GlcNAc compositions of the invention are discussed infra.

The endothelin antagonist or other antitumor agent may be covalently attached to the exposed primary amines of deacetylated p-GlcNAc by, for example, chemical attachment utilizing bi-functional cross-linking reagents that act as specific-length chemical spacers. Such techniques are well known to those of skill in the art, and may resemble, for example, the methods of Davis and Preston (Davis, M. and Preston, J. F. 1981, Anal. Biochem. 116:404–407) and Staros et al. (Staros, J. V. et al., 1986, Anal. Biochem. 156:220–222). For example, in the case of peptide-based compounds, carboxylic residues on the peptide to be attached to the deacetylated or partially deacetylated p-GlcNAc may be activated and then crosslinked to the p-GlcNAc. Activation may be accomplished, for example, by the addition of a solution such as carbodiimide EDC (1-ethyl-3-(3-dimethylaminopropyl)carbodiimide) to a peptide solution in a phosphate buffer. Preferably, this solution would additionally contain a reagent such as sulpho-NHS (N-hydroxysulphosuccinimide) to enhance coupling. The activated peptide may be crosslinked to the deacetylated p-GlcNAc by mixing in a high pH buffer, such as carbonate buffer (pH 9.0–9.2).

The biological activity of the attached molecule can be maintained by varying the length of the linker molecule (e.g., the bi-functional crosslinking compound) utilized to attach the molecule to the p-GlcNAc. An appropriate linker length for a given molecule to be attached which will not alter the biological activity of the attached molecule can routinely be ascertained. For example, the biological activity (e.g., a therapeutically effective level of biological activity) of a molecule which has been attached via a linker of a given length can be tested by utilizing well-known assays specific for the given molecule being attached. Additionally, in order to maintain the biological activity of the molecule being attached, it may be necessary to utilize a linker which can be cleaved by an appropriate naturally occurring enzyme to release the attached molecule. Assays commonly employed by those of skill in the art may be used to test for the retention of the biological activity of the particular molecule being attached to ensure that an acceptable level of activity (e.g., a therapeutically effective level activity) is retained.

Alternatively, peptide-based or non-peptide-based endothelin antagonists, alone or in combination with other antitumor agents, may be mixed with or non-covalently attached to p-GlcNAc and/or its derivatives to form the compositions of the invention, using techniques well known to those of skill in the art. For example, a molecule or molecules of choice, e.g., an endothelin antagonist, may be mixed with suspensions of p-GlcNAc, with a deacetylated or partially deacetylated p-GlcNAc solution, with a deacetylated or partially deacetylated p-GlcNAc salt solution, e.g. with a p-GlcNAc-lactate solution (partially or fully deacetylated), or with any p-GlcNAc derivative solution. The mixtures may optionally be lyophilized. Molecules become non-covalently bound to the p-GlcNAc matrices following lyophilization, presumably via hydrophobic, electrostatic and other non-covalent interactions. Such p-GlcNAc formulations are very easy to produce. Further, such formulations can effectively be achieved with a wide variety of molecules having a broad spectrum of physical characteristics and water solubility properties, ranging from the most hydrophobic to the most hydrophilic. Upon attachment of the molecule or molecules, assays commonly employed by those of skill in the art to test the activity of the particular non-covalently attached molecule or molecules can be used to ensure that an acceptable level of activity (e.g., a therapeutically effective activity) is achieved with the attached molecule.

In addition, endothelin antagonists, alone or in combination with other antitumor agents, can be encapsulated in the p-GlcNAc using methods known in the art. For example, one method for achieving encapsulation can involve the procedure outlined by Hwang et al. (Hwang, C. et al. in Muzzarelli, R. et al., eds., 1985, "Chitin in Nature and Technology", Plenum Press, pp. 389–396) which is incorporated by reference in its entirety. Encapsulation can also be achieved, for example, by following a modification of the acid treatment/neutralization variation of the chemical/ biological purification method presented above. Rather than raising the pH of the p-GlcNAc solution to approximately neutral pH range (i.e., approximately 7.4), one may create a basic pH environment, by raising the pH to approximately 9.0 after the purification of the p-GlcNAc is completed. At a more basic pH, the structure of the p-GlcNAc, or a derivative thereof, assumes a more three-dimensional or "open" configuration. As the pH is lowered, the molecule's configuration reverts to a more compact, "closed" configuration. Thus, a compound or drug of interest, such as an endothelin antagonist, may be added to a p-GlcNAc solution at a high pH, then the pH of the p-GlcNAc/drug suspension may be lowered, thereby "trapping" or encapsulating the drug of interest within a p-GlcNAc matrix. Upon encapsulation of the molecule, assays commonly employed by those of skill in the art may be utilized to test the activity of the particular molecule or molecules encapsulated, thereby ensuring that an acceptable level of biological activity (e.g., a therapeutically effective activity) is retained by the encapsulated molecule.

An example of the preparation of an EA/p-GlcNAc composition of the invention is set forth in Example Section 10, infra, wherein an endothelin antagonist is mixed with a p-GlcNAc lactate gel. Alternatively, an EA composition (without an accompanying p-GlcNAc) can be prepared, e.g., by dissolving the endothelin antagonist in PBS, HBSS or as described by manufacturer's instructions, and adjusting the solution to the desired concentration.

The compositions of the invention, including EA/p-GlcNAc compositions, may be formulated for administration as pharmaceutical compositions, e.g., by inhalation or insufflation (either through the mouth or the nose) or oral, buccal, parenteral or rectal administration. According to a preferred embodiment, the EA/p-GlcNAc composition of the invention is administered by injection in the form of a gel as described in Example Section 10, infra. In the embodiment of the invention wherein the pharmaceutical composition comprises the administration of an endothelin antagonist, e.g., a non-peptidyl endothelin antagonist such as a pyrimidyl sulfonamide, for the treatment of proliferative disease, e.g., cancer, the composition may comprise a therapeutically effective amount of the endothelin antagonist in combination with a pharmaceutically acceptable carrier.

For oral administration, the pharmaceutical compositions may take the form of, for example, tablets or capsules prepared by conventional means with pharmaceutically acceptable excipients or carriers such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The p-GlcNAc may be used in place of, or in addition to, the excipients, carriers and fillers. Tablets may be coated using p-GlcNAc using methods well known in the art.

Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

5.4 Uses of the Compositions and Methods of the Invention

Biomedical uses of the compositions of the invention include their use as drug delivery systems for endothelin antagonists as well as other therapeutic agents such as other antitumor agents. The p-GlcNAc-containing formulations of the invention provide additional benefits compared to known drug formulations, including, for example, increased effectiveness, reduced toxicity and improved bioavailability. In fact, there are numerous advantages in using the p-GlcNAc-based drug delivery systems of the invention. For example, traditional drug administration by injection is commonly used with proteins and many other drugs. However, repeated doses lead to oscillating blood drug concentrations and affect patient comfort and compliance. Oral administration can be advantageous since it allows for a more varied load of the drug to be released and is less discomforting to the patient. However, proteins and other compounds are denatured and degraded in the stomach.

An improved oral administration, however, is achieved by the p-GlcNAc-containing compositions of the invention by providing a protective environment for the drug once administered. For example, the p-GlcNAc protects a peptide-based endothelin antagonist from the acidic and enzymatic environment of the stomach. The p-GlcNAc system releases the compound via diffusion and/or encapsulation degradation once it reaches the intestinal region, where it is effectively absorbed into the blood stream. These p-GlcNAc systems of the invention can be used, for example, to deliver proteins as well as many other compounds. Liposomes coated with p-GlcNAc derivatives or p-GlcNAc derivatives-alginate encapsulations are preferred for such oral delivery methods.

In addition, upon introduction of the compositions of the invention into a patient, the p-GlcNAc biodegrades over time, such that the attached or enclosed compounds are gradually released into the bloodstream of the patient, thus providing a method for controlled, slow-release drug delivery.

Deacetylated or partially deacetylated p-GlcNAc species may be produced having a predictable rate of biodegradability. For example, the percentage of deacetylation affects the rate at which the p-GlcNAc species degrades. Generally, the higher the percentage of deacetylation, the faster the rate of biodegradability and resorption will be. Thus, the degree of p-GlcNAc biodegradability and the in vivo rate of resorption may be controlled during the p-GlcNAc's production.

p-GlcNAc materials having such controllable biodegradability rates may be formulated into membranes, gels, sponges, microspheres, fibers and the like. According to a preferred embodiment of the invention, a 100% deacetylated or partially deacetylated p-GlcNAc having a predictable rate of biodegradability may be utilized.

The p-GlcNAc/drug compositions of the invention may be delivered to a patient via a variety of routes using standard procedures well known to those of skill in the art. For example, such delivery may be site-specific, oral, nasal, intravenous, subcutaneous, intradermal, transdermal, intramuscular or intraperitoneal administration. With respect to site-specific delivery, administration methods may include, but are not limited to injection, implantation, arthroscopic, laparoscopic or similar means. p-GlcNAc membranes and/or gels as well as microspheres and sponges are preferred for such site-specific delivery methods.

As noted supra, the p-GlcNAc of the compositions of the invention may be formulated into membranes, gels, sponges, microspheres, fibers, and the like. These p-GlcNAc products adhere and mold to tissues, both soft and hard tissues, in the human body with no need for suturing. The p-GlcNAc materials may, for example, be applied during general or minimally invasive surgery, such as laparoscopic surgery.

According to a preferred embodiment of the invention, the p-GlcNAc is in the form of a gel in which the endothelin antagonist and/or other antitumor agent is dissolved or otherwise incorporated. p-GlcNAc-based gels and membranes have a variety of applications as therapeutic drug delivery systems, e.g., to provide site-specific slow-release delivery directly to a tumor or to the region vacated by a tumor following surgery. Such an immobilized slow-release composition can act as an important initial defensive procedure after surgery. In addition, such antitumor drug delivery systems can be particularly useful in treating tumors which are totally or partially inaccessible to surgery such as, e.g., certain brain tumors.

The EA/p-GlcNAc compositions of the invention are therefore useful as therapeutic drug delivery systems for the treatment of cancer and other proliferative diseases. These compositions can additionally include other antitumor agents, which can be attached to, or encapsulated within, the p-GlcNAc of the invention to provide a synergistic effect. Such antitumor agents are well known to those of skill in the art, and include, but are not limited to, the following categories and specific compounds: alkylating agents, anti-metabolite agents, anti-tumor antibiotics, vinca alkaloid and epidophyllotoxin agents, nitrosoureas, enzymes, synthetics, hormonal therapeutic biologics and investigational drugs.

Such alkylating agents may include, but are not limited to, nitrogen mustard, chlorambucil, cyclophosphamide, ifosfamide, melphalan, thiptepa and busulfan.

Antimetabolites can include, but are not limited to, methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide.

Nitrosoureas include carmustine, lomustine, semustine and streptozocin. Enzymes can include, but are not limited, to L-asparagine. Synthetics can include, but are not limited to Dacrabazine, hexamethylmelamine, hydroxyurea, mitotane procabazine, cisplatin and carboplatin.

Hormonal therapeutics can include, but are not limited to corticosteriods (cortisone acetate, hydrocortisone, prednisone, prednisolone, methyl prednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole).

Biologics can include, but are not limited to interferons, interleukins, tumor necrosis factor, and biological response modifiers.

Investigational Drugs can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Menaril, Morpholino anthracyclines, Pirarubicin, and SM-5887; microtubule spindle inhibitors, such as Amphethinile, Navelbine, and Taxol; the alkyl-lysophospholipids, such as BM41-440, ET-18-OCH$_3$, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; and Toremifene, Trilosane, and zindoxifene.

Antitumor drugs that are radiation enhancers are preferred for instances in which radiation therapy treatment is to be prescribed, either in lieu of, or following surgery. Examples of such drugs include, for example, the chemotherapeutic agents 5'-fluorouracil, mitomycin, cisplatin and its derivatives, taxol, doxorubicin, actinomycin, bleomycins, daunomycins, and methamycins.

Additional synergistic effects can be obtained using the EA/GlcNAc compositions of the invention in combination with two or more other antitumor agents such as thioguanine combined with cytosine arabinoside (ara-C) for the improved treatment of acute nonlymphocytic leukemia, tamoxifen with cisplatin for breast cancer, and prostaglandins with cisplatin for breast and prostate cancer. Many other synergistic combinations of anti-cancer drugs, known to those of skill in the art, may be used with the EA/p-GlcNAc and EA/p-GlcNAc derivative formulations of the invention.

Additionally, the use of the p-GlcNAc-containing compositions of the invention is desirable given that the p-GlcNAc polymer has chemical properties and characteristics making possible the formulation and delivery of some drugs that have heretofore been difficult to formulate and deliver. For example, taxol, a microtubule spindle inhibitor drug used to treat breast cancer, is hydrophobic and requires the addition of polyoxyethylated castor oil in order to solubilize it as a liquid infusion for intravenous delivery. The hydrophobic nature of taxol makes it an ideal compound for formulation with p-GlcNAc polymer materials for topical controlled release delivery. U.S. Pat. No. 5,635,493 at Section 23, incorporated herein by reference, presents such a p-GlcNAc/taxol formulation. Additional targets for p-GlcNAc antitumor systems include, but are not limited to, skin, GI tract, pancreatic, lung, breast, urinary tract and uterine tumors, and HIV-related Kaposi's sarcomas.

Because the p-GlcNAc materials of the invention are themselves immunoneutral, in that they do not elicit an immune response in humans, such p-GlcNAc devices, as described above, comprising p-GlcNAc membranes, 3D porous matrices and/or gels that harbor immobilized drugs, may deliver such drugs in a manner such that there is no immune response. Certain additional materials, such as natural alginates and synthetic polymers, may be used in some cases to construct such devices in combination with the p-GlcNAc material. For instance, a polymeric delayed-release drug delivery system can be manufactured in a manner similar to that suggested by A. Polk (Polk, A. et al., 1994, J. of Pharmaceutical Sciences, 83(2):178–185). In such a procedure, deacetylated p-GlcNAc is reacted with sodium alginate in the presence of calcium chloride to form microcapsules containing the drug to be delivered and released under appropriate conditions and over a certain lapse of time.

The therapeutically effective doses of any of the drugs or agents described above, in conjunction with the p-GlcNAc-based systems described herein, may be routinely determined using techniques well known to those of skill in the art. A "therapeutically effective" dose refers to that amount of the compound sufficient to result in amelioration of symptoms of the processes and/or diseases described herein.

Toxicity and therapeutic efficacy of the drugs can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. According to a preferred embodiment, the dose range of the endothelin antagonists used in the compositions of the invention is from about 1 mg/kg to about 100 mg/kg.

Further, the doses of many of the antitumor drugs listed above are well known to those of skill in the art and can be easily found in such compendia as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publishers, THE CHEMOTHERAPY SOURCE BOOK, Williams and Wilkens Publishers, online services such as the Cancer Lit®, U.S. National Cancer Institute database, as well as reports of pharmacological studies such as "A MultiCenter Randomized Trial of Trial of Two Doses of Taxol" Nabholtz, J. M., Gelmon, K., Bontenbal, M. et al. Medical Education Services Monograph—1994 Bristol-Myers Squibb Company Publication; "Randomized Trial of Two Doses of Taxol in Metastatic Breast Cancer: An Interim Analysis" Nabholtz, J. M., Gelmon, K., Bontenbal, M., et al. 1993, Proc. Am. Clin. Oncol., 12:60. Abstract 42.

The dose ranges for antitumor drugs in the compositions of the invention may be lower than, equal to or greater than the typical daily doses prescribed for systemic treatment of patients. For example, dosages of 5'-FU equivalent to 50% of the standard dosages used to treat colorectal cancer with 5'-FU in humans (300–450 mg/m² i.v. daily for 5 days) resulted in an 80–90% reduction in volume of ectopic HT29 colon cancer tumor implants in scid mice. The use of the p-GlcNAc membrane as a drug delivery matrix for the administration of 5'-FU reduced the dosage required to dramatically reduce tumor volume by 50% as compared to intravenous control animals. Details regarding this data can be found in Example Section 21 of U.S. Pat. No. 5,635,493, which is incorporated herein by reference. In cases where higher doses are required, these higher doses may be tolerated in that the drugs are delivered locally at the site of a tumor, and therefore, other tissues, including blood cells, are not as readily exposed to the drugs.

Certain antitumor agents are vesicants, including dactinomycin, daunomycin, doxorubicin, estramustine, mechlorethamine, mitomycin C, vinblastine, vincristine and vindesine; while certain antitumor drugs are irritants, including carmustine, decarbazine, etoposide, mithrmycin, streptozocin and teniposide. Vesicants and irritants cause adverse side-effects including extravasation and irritation of tissues with pain, redness, swelling, and other symptoms. Further, tissue necrosis can result from some of the side effects. The p-GlcNAc membrane and gel materials of the compositions of the invention used for the topical, controlled release of antitumor drugs have wound healing properties. Normal tissues that are in contact with vesicant or irritant antitumor drugs delivered by the p-GlcNAc membrane and gel formulations of the invention are, therefore, not as readily damaged and will heal faster due to the active healing effects of the p-GlcNAc component of the p-GlcNAc-containing compositions of the invention.

6. EXAMPLE

Purification of p-GlcNAc Using the Mechanical Force Purification Method

In this section, p-GlcNAc was purified using the Mechanical Force technique described in Section 5.1, supra.

6.1 Materials and Methods/Results

Diatom culture conditions: The diatom species *Thalassiosira fluviatilis* was grown in culture according the procedures described in U.S. Pat. No. 5,635,493, incorporated herein by reference.

SEM procedures: The SEM techniques used here were as follows: A Zeiss 962 instrument was utilized with an accelerating voltage of 10 kv, and a working distance of 15 mm. Polaroid type 55 p/n (u4) was utilized at various magnifications, as indicated. Sample coat:carbon coat (100 Å) & 100 Å aupd.

(a) Specimen preparation: For primary fixation, the culture growth medium was replaced with 2% glutaraldehyde in Eagle's DMEM without serum. Several changes were performed to ensure a complete transition from growth media to fixative. Fixation proceeded for 0.5 hours at room temperature. Cover slips were transferred to fresh vials containing 2% Glutaraldehyde in 0.1M Na Cacodylate at pH 7.2 with 0.1M Sucrose and fixed for a further 1.5 hours at room temperature.

p-GlcNAc Purification procedure: p-GlcNAc was purified from the diatom culture by utilizing the Mechanical Force technique described in Section 5.1, supra. Specifically, the p-GlcNAc fibers were separated from the diatom cell bodies by subjecting the contents of the culture to three short bursts of top speed mixing motion in a Waring blender. Total time of the three bursts was about one second. The resulting suspension was centrifuged at 3500 rpm in a Sorvall GS-4 fixed angle rotor, for 20 minutes at about 10° C. The supernatant was decanted, and centrifuged again, this time at 4000 rpm, in a Sorvall GS-4 fixed angle rotor for 20 minutes at about 10° C. Once again, the supernatant was decanted and centrifuged at 4000 rpm at 10° C. The final supernatant of the third centrifugation was clear, with little, if any, visible flocs floating in the liquid. The clear supernatant was decanted into a Buchner filtration unit equipped with a Supor-800 polyether sulfone filter membrane with 0.8 $\mu$m pore size (Gelman, Inc.), suction was then applied and the liquid was filtered from the fiber suspension, allowing the fibers to be collected on the membrane. The collected fibers were washed with 1 liter of distilled, deionized $H_2O$ at 70° C. When almost all of the water had been drained, fibers were washed, with suction, with 1 liter of 1 N HCl at 70° C. When most of the acid solution had been drained, the fibers were washed with 1 liter of distilled, deionized $H_2O$ at 70° C., using suction. When most of the wash water had been drained, the fibers were washed with 1 liter of 95% ethanol at room temperature, and vacuum was applied. The filter membrane on which the white fiber membrane had been collected was then removed from the filtration unit and the membrane and its membrane support was dried in a drying oven at 58° C. for 20 minutes, after which the membrane and its support was placed in a desiccator for 16 hours.

Following this purification procedure, the yield of p-GlcNAc from a 1000 ml culture was 6.85 milligrams per liter of diatom culture.

7. EXAMPLE

Purification of p-GlcNAc Using the Biological/Chemical Purification Method

In this section, p-GlcNAc was purified using two of the Chemical/Biological techniques described in Section 5.1, supra. Briefly, p-GlcNAc was purified via HF treatment, in one case, and via acid treatment/neutralization in the second case.

7.1 Materials and Methods/Results

Diatom culture conditions: The diatom species *Thalassiosira fluviatilis* was grown in a culture according to the procedures described in U.S. Pat. No. 5,635,493, incorporated herein by reference.

SEM procedures: The techniques utilized in this study were as described supra.

Purification procedure: First, p-GlcNAc was purified by HF treatment. Specifically, under a fume hood, 2.42 ml of a 49% (29 N) HF solution was added to the diatom contents of the culture, at room temperature, for each 1000 ml of the volume of the original cell culture, resulting in a 0.07 M HF solution. The mixture was then shaken vigorously for about seconds, causing persistent foam to appear over the liquid. The container was allowed to stand undisturbed for 5–6 hours to allow heavy particulates to settle. At the end of this time, a layer of foam had formed, while the liquid itself was divided into two strata: first, a narrow, very dark green layer resting on the bottom of the container below a second, much lighter colored grayish-green and murky phase which represented perhaps 85–90% of the total volume of liquid. The foam layer was carefully siphoned off, using a capillary glass tube and vacuum suction. The grayish cloudy supernatant was then siphoned off, with care being taken not to disturb the dark bottom layer, which consisted mainly of settled cell bodies, and was transferred to a separate plastic container. The grayish cloudy supernatant was allowed to stand undisturbed for an additional 16 hours. The liquid was initially almost colorless, light grey, but not transparent. After 16 hours settling time, a small amount of foam remained on top of the main body of liquid and a small amount of green matter had settled on the bottom of the container. The liquid was lighter in color, but still not transparent. The foam on top of the liquid was siphoned off as before. The main body of liquid was then carefully siphoned off, leaving behind the small amount of settled green material at the bottom of the container. The liquid which had thus been isolated, contained the majority of the p-GlcNAc fibers and some impurities.

To remove proteins and other unwanted matter liberated by the diatoms during the preceding steps in the procedure from the fiber-containing liquid, the suspension of fibers and cell remnants was washed with sodium dodecyl sulfate (SDS). Specifically, the necessary volume of a 20% SDS solution was added to make the final concentration of the liquid 0.5% SDS by volume. The container holding the liquid was sealed, secured in a horizontal position on a shaking machine, and agitated for 24 hours at about 100 shakes a minute. Soon after shaking began, large flocs of white p-GlcNAc fibers appeared in the suspension, and a considerable amount of foam accumulated in the head space of the containers. At the end of the SDS washing, the contents of the containers were transferred to a Buchner filtration equipment provided with a Supor-800 polyether sulfone filter membrane, with 0.8 micron pore size (Gelman, Inc.). The liquid was filtered with suction, and the p-GlcNAc fibers in the liquid were collected on the filter membrane.

The p-GlcNAc fibers collected on the filter membrane were then washed further. First, the fibers were washed with hot (70° C.) distilled, deionized $H_2O$, using three times the volume of the original suspension. With a water jet using distilled, deionized $H_2O$, the white fiber clumps collected on the filter membrane of the Buchner filter were transferred to a Waring blender, and the fiber clumps were disintegrated with about 10 short mixing bursts. The suspension of disintegrated fibers was transferred to a Buchner filter funnel equipped with a polyether sulfone filter membrane as described above, and the liquid was removed under suction. The collected fibers were washed with 1000 ml of hot (70° C.) 1N HCl solution, and subsequently further washed with 1000 ml hot (70° C.) distilled, deionized $H_2O$. Finally, the fibers were washed with 1000 ml 95% ethanol at room temperature, and filtered to dryness. The fiber membrane and the filter membrane supporting the fiber membrane were then dried in a drying oven at 58° C. for 20 minutes. The membrane and membrane support was then placed in a desiccator for 16 hours. The membrane was then carefully detached from the filter membrane.

Second, p-GlcNAc was purified by using the acid treatment/neutralization method described in Section 5.1, supra. Specifically, the p-GlcNAc was processed as described earlier in this Section, until prior to the SDS wash step, at which point the solution was neutralized to a pH of approximately 7.0 by the addition of a 2.9M Tris solution.

The p-GlcNAc yield from this particular purification procedure was 20.20 milligrams per liter of diatom culture, although, on average, approximately 60 milligrams per liter diatom culture are obtained. An SEM micrograph of a membrane formed as a result of the acid treatment/neutralization purification procedure is shown in FIG. 3.

8. EXAMPLE p-GlcNAc Deacetylation

A p-GlcNAc membrane was suspended in an aqueous 50% NaOH solution. The suspension was heated at 80° C. for 2 hours. The resulting deacetylated membrane was dried and studied by scanning electron microscopy, as shown in FIG. 5.

9. EXAMPLE p-GlcNAc Reformulation

A p-GlcNAc membrane (16.2 mg) was dissolved in 1 ml of a dimethylacetamide solution containing 5% LiCl. The p-GlcNAc-containing solution was placed in a syringe and extruded into 50 ml of pure water to precipitate the fibers. The resulting fiber material was studied using scanning electron microscopy, as shown in FIG. 6.

10. EXAMPLE

Preparation of an EA/p-GlcNAc Composition of the Invention

Ro61-0612/001 (also referred to herein as "Ro61") is a non-specific, non-peptide-based endothelin antagonist with the structure as depicted in Formula I, supra. Its chemical name, in salt form, is 5-Isopropyl-pyridine-2-sulfonic acid [6-(2-hydroxy-ethoxy)-5-(2-methoxy-phenoxy),-2-[2-(1H-tetrazol-5-yl)-pyridin-4-yl]-pyrimidin-4-yl]amide sodium salt (1:2) and its molecular weight is 649.59. Its solubility in water is greater than 3%. Ro61's binding inhibitory potency ($IC_{50}$) as to the ETA receptor is 1–20 nM and as to the ETB receptor is 20–30 nM. Its functional inhibitory potency (pA2) with respect to the ETA receptor is 9.5 and with respect to the ETB receptor is 7.7. Its recommended dose in vivo is 1–30 mg/kg iv or ip. Its recommended dose in vitro is $10^{-9}$ to $10^{-5}$ M.

Ro61 for use in a composition of the invention was provided initially as a lyophilized powder from Acetelion Ltd, Allschwil, Switzerland, which was suspended in sterile water, and the pH was adjusted to 4.0 with sterile hydrochloric acid. Alternatively, Ro61 can be synthesized using techniques known in the art.

A p-GlcNAc fiber slurry was prepared as follows: p-GlcNAc prepared by the biological/chemical method described in Example Section 7 supra was resuspended in distilled-deionized water and agitated to form a fibrous suspension or slurry of about 1 mg/ml. The fiber slurry was then oven dried at 60° C. for 2 h to form p-GlcNAc polymer membranes. The membranes were deacetylated in 40% NaOH solution at 80° C. for 2 h. When the membranes reached 100% deacetylation, they were washed with distilled-deionized water until a pH of 7.0 was achieved.

The washed deacetylated membranes were then converted to p-GlcNAc lactate salt in the presence of lactic acid essentially as described in U.S. Pat. No. 5,623,064 incorporated herein by reference. Briefly, the deacetylated p-GlcNAc was suspended in an organic medium such as 2-propanol (containing 10% water) so as to wet all of the deacetylated p-GlcNAc material. With stirring, an appropriate amount of 50% aqueous lactic acid solution was added. The lactic acid should be reagent grade, and must be analyzed to determine the exact concentration of available (i.e., non-esterified) lactic acid present. This was generally accomplished by titration with 0.1 N NaOH to the phenolphthalein end-point (pH 7.0). The mixture was allowed to stir for at least two hours at room temperature. Low heat may be added to increase the reaction rate. Reaction time may be extended or the amount of 50% aqueous lactic acid may be increased to ensure that the reaction goes to completion. The suspension was then finely filtered through a Buchner funnel using quantitative ashless filter paper and the material, in the form of a membrane, was washed with anhydrous 2-propanol. The membrane was then allowed to air dry in a fume hood for 2 hours and then placed in an oven at 40° C. overnight.

An EA/p-GlcNAc gel was next prepared for injection by dissolving the p-GlcNAc lactate membranes in distilled-deionized water to the desired concentration, e.g., 2% p-GlcNAc-lactate by weight and adding Ro61 to the solution. The final concentration of Ro61 in the gel was adjusted so that each animal received 3 mg/kg in a 200 μl sample of gel. optionally, a reagent grade propylene glycol (2-propanediol) can be added to the p-GlcNAc solution to a final propylene glycol concentration of between 1–10%. In some cases, a preservative may be added to prevent bacterial and/or fungal contamination. According to other embodiments, concentrations of p-GlcNAc-lactate ranging from 0.1% to 4.0% can be prepared as described above. The viscosity of these preparations increases as the p-GlcNAc-lactate percentage increases, such that formulations having 0.5% of more of the p-GlcNAc-lactate behave as gels.

11. EXAMPLE

Ro61 Inhibition of Melanoma Cell Proliferation in vitro

B16 cells were evaluated for use as an endothelin responsive tumor model system. The B16 cells, i.e., from the B16 murine melanoma cell line (of fibroblastic origin), were obtained from the American Type Culture Collection (Rockville Md.) as a frozen stock. The cells were cultured in complete medium (CM): RPMI 1640 (Irvine Scientific, Santa Ana Calif.) supplemented with 10% heat-inactivated fetal bovine serum (Summit Biotechnologies, Ft. Collins Colo.), penicillin (50 units/ml, streptomycin (50 μg/ml), 2 mM L-glutamine, 0.1 mM MEM nonessential amino acids (Gibco BRL, Gaithesburg Md.), 1 mM sodium pyruvate, and 0.05 mM 2-mercaptoethanol (Sigma Immunochemicals, St. Louis Mo.). The cells were grown at 37° C. in a humidified 5% $CO_2$ incubator and adjusted to $1\times10^5$ cells/ml every second day.

The B16 cells were analyzed for endothelin levels and endothelin receptor (ETR) expression as follows: ET1 in the B16 culture supernatants was measured by a competitive radioimmunoassay (RPA 545, Amersham, Milford Mass.) with radioactive ligand and an ET1-specific antibody. Bound and free ET were reacted with a second antibody phase system followed by magnetic separation. A standard curve was determined by calculating the percentage of bound ligand/zero standard (B/Bo), and the concentration of ET could be read from this standard curve. The recovery from the extraction procedure was 75±5% based upon plasma spiked standards (4-20 fmol/ml). The interassay variation was 10% and the intra-assay variation was 9% for the ET radioimmunoassay procedure.

Using this assay, baseline ET1 levels in 24 h B16 culture supernatants were found to be 1.269 fmol/ml. Addition in the cultures of 10 nM of either an ETA or ETB agonist or both induced increased proliferation of the B16 cells by 137%, 117% and 164% of untreated controls, respectively, with corresponding ET1 levels of 34.01, 1.158, and 34.01 fmol/ml, respectively.

In addition, the B16 cells were determined to express endothelin receptors via immunofluorescence staining using the intracellular flow cytometry kit from Pharmingen with anti-cytoplasmic endothelin receptor antibodies, i.e., directed against the cytoplasmic region of the receptor (Research Diagnostics Inc., Flanders N.J.) and sheep antimouse IgG isotypic antibody controls (Sigma Immunchemicals, St. Louis Mo.). According to this procedure, the B16 cells were washed in Cytofix/Cytoperm buffer (from the Pharmingen kit) and incubated for 20 min with a permeabilization solution (0.1% Triton X100 in 0.1% sodium citrate). Cells were then incubated at 4° C. in the dark for 30 min with primary anti-endothelin receptor or isotype control antibodies, and then washed and incubated an additional 30 min with the secondary FITC-labeled antibody (mouse anti-sheep IgG; Sigma). Cells were visualized and photographed using a Axioplan research microscope (Carl Zeiss Inc. Jena Germany) equipped with a 100 watt mercury light source and a 40× plan-neufluar nal.3 objective.

In contrast to the ETR expression of the B16 cells, normal splenocytes do not show visible levels of ETR as detected by immunofluorescence as described above. Due to the facility of splenocyte isolation and culture, they were therefore used as control cells to assess the effects of Ro61 on cell proliferation. Splenocytes were harvested from female 6–8 week old C57BL/6 (H-2b) mice (Jackson Laboratories, Bar Harbor Mass.) as follows: spleens were removed, placed in CM, and their cells dispersed with a 3 cc syringe plunger. The cell suspension was then filtered through a 70 μm cell strainer and erythrocytes were lysed with ammonium chloride lysis solution (prepared by mixing 9 parts 8.3 g/L ammonium chloride; 1 part 20.59 g/L Tris, pH 7.65 immediately before use). The splenocytes were then washed and resuspended in CM.

Ro61 was obtained as a lyophilized powder from Acetelion Ltd, Allschwil, Switzerland as described above and proliferation assays performed to assess the effect of Ro61 on B16 cell proliferation. The cell proliferation assay was performed as follows: Ro61 in HBSS was added at increasing concentrations to a 96 well culture plate. B16 cells or control splenocytes as described above were then added to the wells at a concentration of $10^5$ cells per well and grown for 72 h. Cell proliferation was assayed using the CellTiter 96 kit for non-radioactive cell proliferation measurement (Promega, Madison Wis.) as follows: Briefly, cells were incubated with 15 ml of MTT dye (from Promega kit) for 4 h after which formazan crystal formation was visible. Crystals were dissolved in 50 ml of solubilization/stop solution (from Promega kit) for 30 min at room temperature and color changes were measured as OD 570 nm. Background OD at 630 was subtracted automatically. Mean values of triplicate wells were determined. Cell proliferation or death was also recorded by photography of light microscopy at 40× focal power.

The inhibitory effect of Ro61 on the B16 melanoma cells is depicted in FIG. 7. Proliferation of Ro61-treated cells is expressed as a percentage of untreated control cells. Mean values of triplicate wells were determined. As can be seen in FIG. 7, Ro61 inhibited the proliferation of the B16 cells (closed circles) but did not inhibit the normal splenocytes (open circles). Moreover, when Ro61 was added at increasing concentrations to the cells in culture, a dose dependent inhibition was observed. This effect was seen at concentrations of 0.1 μM (22% inhibition compared to untreated controls) and was maximal at 10 μM (83% inhibition). Microscopically, at the highest concentration of Ro61, the B16 cells no longer had a normal fibroblast-like spindle shape but were round and sparse with poor viability (see FIGS. 12A–12B). In contrast to this, the splenocytes were only minimally affected by the addition of even the highest concentration of Ro61 (10 μM).

It was also found that endothelin levels in the B16 culture supernatants decreased in a dose dependent manner consistent with antagonism of ETR-mediated ET1 autoinduction, decreasing from 1.12 fmol/ml at 0.5 nM to 0.775 fmol/ml at 10 nM of Ro61 (data not shown).

Since Ro61, an inhibitor of the ET receptor, caused the inhibition of B16 cell proliferation, it was of interest to determine whether the addition of peptide agonists specific for ETA or ETB could reverse this effect. The ETA agonist, BQ-3020-[Ac-[Ala11, 15]-endothelin(6,21)(Novabiochem, catalog no. A1 4534) and the ETB agonist, [Ala$^{1,3,11,15}$]-endothelin1 (Sigma Immunochemicals, St. Louis Mo., catalog no.: E6877) were suspended in HBSS for use. $5\times10^4$ B16 cells were cultured with either the ETA agonist, the ETB agonist, both of these agonists, or neither at a concentration of 10 nM in each well and Ro61 was then added at various concentrations to the wells.

As demonstrated in FIG. 8, Ro61 inhibition of B16 proliferation was prevented by adding ET receptor agonists. Proliferation of Ro61-treated cells is expressed as a percentage of untreated control cells. Mean values of triplicate wells were determined. First, as indicated by the Y axis of FIG. 8 (0 concentration of Ro61), the addition of the ETA agonist (closed triangle) or the ETB agonist (open diamond) alone, or the two agonists in combination (open box), induced the proliferation of the B16 cells. For the ETA agonist, proliferation was 137% of untreated controls, for the ETB agonist, the proliferation was 117% of untreated controls and for the combination of agonists, the proliferation was 164% of untreated controls.

As indicated further in FIG. 8, the addition of these agonists also counteracted the inhibition induced by increasing doses of Ro61. For example, the addition of the ETB agonist at a concentration of 10 nM completely reversed the effects of Ro61 at a concentration of 1 nM and decreased the inhibition of Ro61 at 5 μM by 50%. The ETA agonist was able to significantly reverse the effects of 5 μM Ro61 (only 12% inhibition of proliferation at 5 μM), which correlated well with the known higher affinity of Ro61 for ETA. The most significant effect was observed with the combination of ETA and ETB agonists inducing proliferation (123% of untreated controls) even with addition of 0.1 μM Ro61. These dose dependent findings defined an endothelin receptor-mediated proliferation response for the murine B16 cells that can be inhibited by an ETR antagonist.

12. EXAMPLE

Ro61 Induction of B16 Melanoma Tumor Apoptotic Cell Death

The above in vitro studies indicated that Ro61 treatment not only contributed to an inhibition of cell proliferation but that there was a significant component of cell death or necrosis present. Therefore, we studied the effect of Ro61 on B16 apoptotic cell death.

B16 cells were grown in CM in 25 ml culture flasks, with or without 1 μM Ro61, at 37° C. in a 5% $CO_2$ incubator for up to 72 h. Cells were assayed for apoptosis or cell death using the Fluorescein In Situ Cell Death Detection Kit (Boehringer Mannheim, Mannheim, Germany) as follows: Briefly, cells were trypsinized and washed with PBS containing 1% bovine serum albumin (BSA). After fixing with a 4% paraformaldehyde solution in PBS (pH 7.4) for 30 min, cells were permeabilized with a solution of 0.1% Triton X100 in 0.1% sodium citrate for 2 min on ice. Cells were then washed and labeled with TUNEL reaction mixture (Boehringer kit) for 1 h at 37° C. and washed. Fluorescence was analyzed on a Coulter EPICS XL flow cytometer (Coulter, Miami Fla.). Measurements were compared to a positive control using 100 μg/ml of DNase I (Boehringer Mannheim, Mannheim, Germany) for 10 min at room temperature to induce double stranded DNA breaks.

As depicted in FIG. 9, the endothelin antagonist Ro61 induced apoptosis in B16 melanoma cells in culture. For example, the addition of 1 μM of Ro61 to the B16 cells led to an increase in the percentage of cells undergoing apoptosis as compared to untreated controls. The increase in percentage of cells positive by the above-described TUNEL assay was detectable as early as 24 h and was still detectable at 48 h. At 72 h, which is the normal doubling time of B16 cells, no apoptotic effect of Ro61 was measured, suggesting the loss of inhibitory effect after 3 days in culture. These results established the presence of apoptotic cell signaling mediated through the ETR which can be induced by an ETR antagonist. Thus, apoptosis is contributing at least in part to the inhibition of cellular proliferation and the cell death observed.

13. EXAMPLE

Inhibition of B16 Melanoma Intraperitoneal Metastases in vivo by an Endothelin Antagonist or an EA/p-GlcNAc Composition of the Invention The striking effects of Ro61 on B16 cells in vitro led to further studies to evaluate the impact of ETR antagonism on in vivo tumor growth utilizing an agressive intraperitoneal (IP) B16 melanoma metastases model. Thus, female C57BL/6 mice were injected intraperitoneally with $5\times10^4$ B16 cells in 100 ml HBSS. One day later, the mice were injected with 100 μl of either HBSS alone (no treatment), HBSS containing 3 mg/kg of Ro61 (administered daily), HBSS containing 30 mg/kg of Ro61 (administered daily), p-GlcNAc gel (2%) alone, or p-GlcNAc gel (2%) containing 3 mg/kg of Ro61.

Animals in the groups treated with HBSS containing either 3 mg/kg or 30 mg/kg of Ro61 alone received daily i.p. injections while all of the other groups were treated only once. The p-GlcNAc gel alone that was utilized in this experiment was prepared as indicated in Example Section 10, supra, minus addition of the Ro61. The Ro61/p-GlcNAc utilized in this experiment was also prepared as detailed above in Section 10. The mice were sacrificed after 7 days and evaluated for the presence of intraperitoneal metastatic disease. More specifically, individual metastases were counted under a dissecting microscope for each animal on the peritoneal surface, mesentery, liver, spleen, and pancreas. Studies were conducted under double blind conditions. Photographs of the peritoneum and digestive organs were taken as well as sections of the mesentery, liver, spleen and pancreatic fat and peritoneum for histological analysis by H and E as well as melanin staining.

This study indicated that injection of one dose of Ro61 alone in HBSS at 1.8 mg/dose per mouse (data not shown) or daily injections of Ro61 at a low dose, e.g., 3 mg/kg, for 6 days did not significantly lower the mean number of metastases per animal. However, as demonstrated in FIG. 10, daily injections of high doses of Ro61 alone at 30 mg/kg did significantly decrease the mean number of metastases one week after tumor injection—109±58 with high-dose Ro61 versus 286±42.6 in untreated controls with $p<0.002$.

In addition, the slow release of a single low dose of Ro61 (3 mg/kg) in a p-GlcNAc matrix almost abolished the appearance of metastases at 7 days post tumor injection— mean number of metastases 4.6±1.8. Interestingly, the p-GlcNAc matrix alone also significantly reduced the number of metastases—125±42.

14. EXAMPLE

Long Term Survival of C57BL/6 Mice after Intraperitoneal B16 Melanoma Challenge with an Endothelin antagonist Alone or an EA/p-GlcNAc Composition of the Invention We next evaluated endothelin antagonism therapy in long term survival experiments in vivo. The results are shown in FIG. 11. Female C57BL/6 mice were injected intraperitoneally with $5\times10^4$ B16 cells in 100 ml HBSS. Animals were randomly separated into 4 groups for either of the following treatments: (a) no treatment (closed boxes);

(b) 100 μl of p-GlcNAc gel alone (crosses); (c) 100 μl of daily HBSS containing 3 mg/kg Ro61 (closed triangles); or (d) 100 μl of p-GlcNAc gel containing 3 mg/kg Ro61 (open boxes). Animals were monitored daily and sacrificed for humane reasons when determined moribund.

It is of interest to note that the B16 melanoma is an extremely virulent tumor, which results in a 0% survival rate consistently within 19–20 days of tumor injection. As indicated in FIG. 10, the injection of p-GlcNAc alone delayed death by 5 days but did not increase the survival rate of the animals. However, the combination of p-GlcNAc and Ro61 at a low dose (3 mg/kg) also delayed death and 33% of the animals showed no evidence of tumor at day 33 after tumor injection. Daily injections of the same low dose of Ro61 alone did not affect survival of the mice.

15. Discussion of Results

The studies conducted herein show direct evidence that inhibiting the binding of endothelins to their receptors can affect the normal proliferation of a murine melanoma cell line, both in vitro and in vivo. The endothelin antagonist, Ro61, is an inhibitor of both the ETA and ETB receptors with an approximately 10-fold higher affinity for ETA. This correlates well with the dose dependent inhibition of melanoma cell proliferation by Ro61 in our experiments, as well as the stronger countering effect to this inhibition obtained by addition of an ETA agonist as opposed to an ETB agonist.

It is also interesting to note that melanoma cells have been shown to express high levels of ET receptors and are more susceptible to endothelin antagonist, e.g., Ro61, inhibition than normal splenocytes, known to have much lower membrane ET receptors. Thus, the evidence in this study points to Ro61 as having an anti-proliferative effect on tumor cells in culture, which inhibition of tumor cell growth is mediated by binding to endothelin receptors that respond to peptide agonists specific for ETA and ETB. In addition, our studies indicate that Ro61, alone or in combination with the p-GlcNAc described herein, significantly reduces metastases in vivo. Moreover, the EA/p-GlcNAc compositions of this invention dramatically increase the survival rate of tumor cell-bearing animals in vivo. The effect of Ro61 appears to involve an apoptotic mechanism of action, which does not contradict some of the known mechanisms of action of endothelins and their signal transduction mechanisms.

We claim:

1. An antitumor composition comprising at least one endothelin antagonist in combination with a poly-$\beta$-1→4-N-acetylglucosamine, said poly-$\beta$-1→4-N-acetylglucosamine comprising about 4,000 to about 150,000 N-acetylglucosamine monosaccharides covalently attached in a :$\beta$-1→4 conformation free of protein, substantially free of other organic or inorganic contaminants, and having a molecular weight of about 800,000 daltons to about 30 million daltons.

2. The composition of claim 1 wherein the endothelin antagonist is a non-specific endothelin antagonist.

3. The composition of claim 1 wherein the endothelin antagonist is an ETA-specific endothelin antagonist.

4. The composition of claim 1 wherein the endothelin antagonist is an ETB-specific endothelin antagonist.

5. The composition of claim 1 wherein the endothelin antagonist is a peptide-based endothelin antagonist.

6. The composition of claim 1 wherein the endothelin antagonist is a non-peptide-based endothelin antagonist.

7. The composition of claim 6 wherein the non-peptide-based endothelin antagonist is a pyrimidyl sulfonamide compound.

8. The composition of claim 7 wherein the pyrimidyl sulfonamide compound is Ro61.

9. The composition of claim 1 wherein the poly-$\beta$-1→4-N-acetylglucosamine comprises a poly-$\beta$-1→4-N-acetylglucosamine derivative wherein at least one N-acetylglucosamine monosaccharide has been deacetylated.

10. The composition of claim 9 wherein the deacetylated monosaccharide is derivatized to a lactate salt.

11. The composition of claim 9 wherein at least about 25% to about 75% of the N-acetylglucosamine monosaccharides have been deacetylated.

12. The composition of claim 1, 9 or 10 wherein the poly-$\beta$-1→4-N-acetylglucosamine is formulated as a gel.

13. The composition of claim 1 or 9 wherein the poly-$\beta$-1→4-N-acetylglucosamine is a mat, string, rope, membrane, fiber or sponge.

14. The composition of claim 12 wherein the endothelin antagonist is dissolved in the poly-$\beta$-1→4-N-acetylglucosamine gel.

15. An antitumor composition comprising at least one endothelin antagonist in combination with a poly-$\beta$-1→4-glucosamine, said poly-$\beta$-1→4-glucosamine comprising about 4,000 to about 150,000 glucosamine monosaccharides covalently attached in a $\beta$-1→4 conformation free of protein, substantially free of other organic or inorganic contaminants, and having a molecular weight of about 640,000 daltons to about 24 million daltons.

16. The composition of claim 15 wherein the endothelin antagonist is a non-specific endothelin antagonist.

17. The composition of claim 15 wherein the endothelin antagonist is an ETA-specific endothelin antagonist.

18. The composition of claim 15 wherein the endothelin antagonist is an ETB-specific endothelin antagonist.

19. The composition of claim 15 wherein the endothelin antagonist is a peptide-based endothelin antagonist.

20. The composition of claim 15 wherein the endothelin antagonist is a non-peptide-based endothelin antagonist.

21. The composition of claim 20 wherein the non-peptide-based endothelin antagonist is a pyrimidyl sulfonamide compound.

22. The composition of claim 21 wherein the pyrimidyl sulfonamide compound is Ro61.

23. The composition of claim 15 wherein the poly-$\beta$-1→4-glucosamine is derivatized to a lactate salt.

24. The composition of claim 15 or 23 wherein the poly-$\beta$-1→4-glucosamine is formulated as a gel.

25. The composition of claim 15 wherein the poly-$\beta$-1→4-glucosamine is a mat, string, rope, membrane, fiber or sponge.

26. The composition of claim 24 wherein the endothelin antagonist is dissolved in the poly-$\beta$-1→4-glucosamine gel.

27. The composition of claim 26 wherein the endothelin antagonist is Ro61 and the poly-$\beta$-1→4-glucosamine gel is a 2% gel.

28. A method for treating a cell proliferative disease comprising administering to a patient a therapeutically effective amount of at least one endothelin antagonist in combination with a poly-$\beta$-1→4-N-acetylglucosamine, said poly-$\beta$-1→4-N-acetylglucosamine comprising about 4,000 to about 150,000 N-acetylglucosamine monosaccharides covalently attached in a $\beta$-1→4 conformation free of protein, substantially free of other organic or inorganic contaminants, and having a molecular weight of about 800,000 daltons to about 30 million daltons.

29. A method for treating a cell proliferative disease comprising administering to a patient a therapeutically effective amount of at least one endothelin antagonist in combination with a poly-$\beta$-1→4-glucosamine, said poly-$\beta$-1→4-glucosamine comprising about 4,000 to about 150,000 glucosamine monosaccharides covalently attached in a $\beta$-1→4 conformation free of protein, substantially free of other organic or inorganic contaminants, and having a molecular weight of about 640,000 daltons to about 24 million daltons.

30. The method of claim 28 or 29, wherein the proliferative disease is cancer.

31. A pharmaceutical composition for the treatment of proliferative disease comprising a therapeutically effective amount of a non-peptide-based endothelin antagonist in a pharmaceutically acceptable carrier.

32. The composition of claim 31, wherein the endothelin antagonist is a pyrimidyl sulfonamide compound.

33. The composition of claim 31, wherein the proliferative disease is cancer.

34. A method for treating cancer comprising administering to a patient a therapeutically effective amount of a non-peptide-based endothelin antagonist in combination with a pharmaceutically acceptable carrier.

35. The method of claim 34, wherein the endothelin antagonist is a pyrimidyl sulfonamide compound.

* * * * *

UNITED STATES PATENT AND TRADEMARK OFFICE
CERTIFICATE OF CORRECTION

PATENT NO. : 6,063,911
DATED : May 16, 2000
INVENTOR(S) : Vournakis et al.

It is certified that error appears in the above-identified patent and that said Letters Patent is hereby corrected as shown below:

<u>Claims,</u>
Please delete claims 31-35.

Signed and Sealed this

Fifth Day of March, 2002

Attest:

Attesting Officer

JAMES E. ROGAN
Director of the United States Patent and Trademark Office